(12) United States Patent
Huang et al.

(10) Patent No.: US 8,008,344 B2
(45) Date of Patent: Aug. 30, 2011

(54) COMPOUNDS FOR THE INHIBITION OF HISTONE DEACETYLASE

(75) Inventors: Chung-Yang Huang, Taipei (TW); Chia-Nan Chen, Taipei (TW); Wei-Jan Huang, Taipei (TW); Chih-Hsiang Huang, Taipei (TW); Li-Ling Chi, Taipei (TW); Chiou-Ping You, Taipei (TW)

(73) Assignee: Naturewise Biotech and Medicals Corporation, Taipei (TW)

( * ) Notice: Subject to any disclaimer, the term of this patent is extended or adjusted under 35 U.S.C. 154(b) by 855 days.

(21) Appl. No.: 11/855,416

(22) Filed: Sep. 14, 2007

(65) Prior Publication Data

US 2009/0076130 A1 Mar. 19, 2009

(51) Int. Cl.
*A61K 31/352* (2006.01)
*C07D 311/32* (2006.01)

(52) U.S. Cl. ........ 514/456; 549/399; 549/400; 549/403; 549/406

(58) Field of Classification Search ............... 549/403, 549/399, 400, 406; 514/456
See application file for complete search history.

(56) References Cited

U.S. PATENT DOCUMENTS

| 6,174,905 B1 | 1/2001 | Suzuki et al. |
| 6,888,027 B2 | 5/2005 | Watkins et al. |
| 7,169,801 B2 | 1/2007 | Bressi et al. |

FOREIGN PATENT DOCUMENTS

| EP | 1640371 A1 | 3/2009 |
| WO | 0138322 | 5/2001 |

OTHER PUBLICATIONS

Yakushijin et al, Heterocycles vol. 4 (4), p. 397-402 (1980).*
Chauhan et al, Planta, Medica, p. 221-222 (1987).*
Phommart et al, J. of Natural Products, vol. 68, p. 927-930 (2005).*
Hsiang-Yu Lin et al.,; Targeting Histone Deacetylase in Cancer Therapy, Journal; Jan. 31, 2006; pp. 397-413; Wiley Periodicals.
Paul A. Marks et al.,; Histone Deacetylase Inhibitors: Inducers of Differentiation or Apoptosis of Transformed Cells; Journal; Aug. 2, 2000; pp. 1210-1216; vol. 92 No. 15; Journal of National Cancer Institute.
Markus Riessland et al.,; The benzamide M344, a novel histone deacetylase inhibitor. . . ; Journal; Apr. 9, 2006; pp. 101-110; Springer-Verlag.
Makoto Minamiyama et al., ; Sodium butyrate ameliorates phenotypic expression in a transgenic mouse model of spinal and bulbar muscular atrophy; Journal; Apr. 21, 2004; vol. 13, No. 11; pp. 1183-1192; Human Molecular Genetics, Oxford University Press.
John P Alao et al.,; Histone deacetylase inhibitor, Trichostatin A induces ubiquitin-dependent cyclin DI degradation in MCF-1 breast cancer cells; Journal; Feb. 20, 2006; pp. 1-11; BioMed Central Ltd.
Written Opinion for Application No. 07116430.5, (2009).
Toshio Fukai et al. Cytotoxic Activity of Low Molecular Weight Polyphenols against Human Oral Tumor Cell Lines, Anticancer Research, 2000, pp. 2525-2536, vol. 20.
Chia-Nan Chen et al., Cornpanson of Radical scavenging Activity, Cytotoxic Effects and Apoptosis Induction in Human Melanoma Cells by Taiwanese Propolis from Different Sources, Evidenced-based Complementary and Alternative Medicine, Aug. 18, 2004, pp. 175-185, vol. 1, Issue 2.
European Search Report for application No. 07116430.5, (2009).
Response to the Communication pursuant to Article 94(3) dated Dec. 2, 2009 for Application No. EP07116430.5.

* cited by examiner

*Primary Examiner* — Bernard Dentz
(74) *Attorney, Agent, or Firm* — WPAT, P.C.; Anthony King

(57) ABSTRACT

The invention relates to a compound represented by the following formula (I):

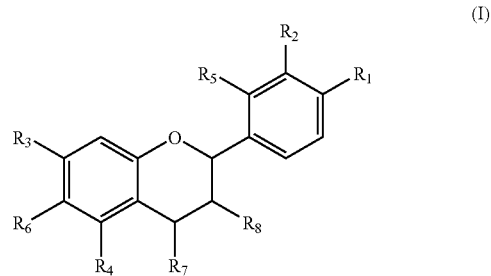

and pharmaceutically acceptable salts, stereoisomers, enantiomers, prodrugs and solvates thereof. The compounds are useful as an agent for enhancing the neurite outgrowth and preventing or treating of diseases associated with HDAC in particular, tumor or cell proliferative diseases. In particular, the compounds of the invention can be used as an agent for anti-neurodegenerative diseases and human spinal muscular atrophy (SMA).

16 Claims, 14 Drawing Sheets

(A)

(B)

(A)

(B)

(A)

(B)

(A)

(B)

COMPOUNDS FOR THE INHIBITION OF HISTONE DEACETYLASE

FIELD OF THE INVENTION

The present invention relates to novel compounds which are useful as the agents for prevention or treatment of diseases associated with histone deacetylase (HDAC), in particular, tumor or cell proliferative diseases. They also can be used as the agents for enhancing the neurite outgrowth. In particular, the compounds of the invention can be used as agents for anti-neurodegenerative diseases and human spinal muscular atrophy (SMA).

BACKGROUND OF THE INVENTION

Eukaryotic DNA is highly organized and packaged in the nucleus. The organization and packaging are achieved through the addition of proteins, including core histones H2A, H2B, H3 and H4, which form a complex structure, the chromatin, together with DNA. The modification of core histones is of fundamental importance to conformational changes of the chromatin. The level of acetylation is related to transcription activity, and then the acetylation induces an open chromatin conformation that allows the transcription machinery access to promoters. Histone deacetylase (HDAC) and histone acetyltransferase (HAT) are enzymes that influence transcription by selectively deacetylating or acetylating the ϵ-amino groups of lysine located near the amino termini of core histone proteins. HDAC is a family of 11 enzymes (isoforms) that may act as master regulators of many diseases, including cancer, because they are involved in the control of gene expression. Disruption of HDACs has been linked to a wide variety of human cancers. HDAC enzymes or isoforms appear to be involved in many different types of cancer.

Histone deacetylase (HDAC) inhibitors are emerging as an exciting new class of potential anticancer agents for the treatment of solid and hematological malignancies. In recent years, an increasing number of structurally diverse HDAC inhibitors have been identified; they inhibit proliferation and induce differentiation and/or apoptosis of tumor cells in culture and in animal models. HDAC inhibition causes acetylated nuclear histones to accumulate in both tumor and normal tissues, providing a surrogate marker for the biological activity of HDAC inhibitors in vivo. The effects of HDAC inhibitors on gene expression are highly selective, leading to transcriptional activation of certain genes such as the cyclin-dependent kinase inhibitor p21WAF1/CIP1 but repression of others. HDAC inhibition not only results in acetylation of histones but also transcription factors such as p53, GATA-1 and estrogen receptor-alpha. The functional significance of acetylation of non-histone proteins and the precise mechanisms whereby HDAC inhibitors induce tumor cell growth arrest, differentiation and/or apoptosis are currently the focus of intensive research. HDAC inhibitors currently in clinical trials have shown activity and represent a class of molecularly targeted anti-tumour agents with potential for efficacy based on a novel mechanism of action.

A review article published in Medicinal Research Reviews, Vol. 26, No. 4, pp. 397-413, 2006 stated that four classes of HDAC inhibitors, short-chain fatty acids, hydroxamic acids, benzamides and cyclic peptides, have been reported. Hydroxamic acid-based hybrid polar compounds (HPCs) are HDAC inhibitors, which induce differentiation at micromolar or lower concentrations (Journal of the National Cancer Institute, Vol. 92, No. 15, Aug. 2, 2000, pp. 1210-1216). U.S. Pat. No. 6,174,905, EP 0847992, JP 258863/96, and Japanese Application No. 10138957 disclose benzamide derivatives that induce cell differentiation and inhibit HDAC. WO 01/38322 discloses additional compounds that serve as HDAC inhibitors. It was reported in Hum Genet, 2006, 120, pp. 101-110 that the benzamide M344 up-regulates SMN2 protein expression in fibroblast cells derived from SMA patients up to 7-fold after 64 hours of treatment. It was reported that sodium butyrate ameliorates phenotypic expression in a transgenic mouse model of spinal and bulbar muscular atrophy (Human Molecular Genetics, 2004, Vol. 13, No. 11, pp. 1183-1192). Trichostatin A, a histone deacetylase inhibitor, was found to induce ubiquitin-dependent cyclin D1 degradation in MCF-7 breast cancer cells (Molecular Cancer 2006, 5:8; this article is available from: http://www.molecular-cancer.com/content/5/1/8). U.S. Pat. No. 7,169,801 disclosed compounds that may be used to inhibit histone deacetylase having the formula Z-Q-L-M or Z-L-M. U.S. Pat. No. 6,888,027 covers a family of Sulphonamide HDAC inhibitors including PXD101. European Patent Number EP 1 301 184 covers the use of valproic acid and derivatives as HDAC inhibitors in the treatment of solid tumors.

However, there is still a need to develop a new class of HDAC inhibitors to prevent or treat cancers.

SUMMARY OF THE INVENTION

The object of the invention is to provide a group of compounds represented by the following formula (I):

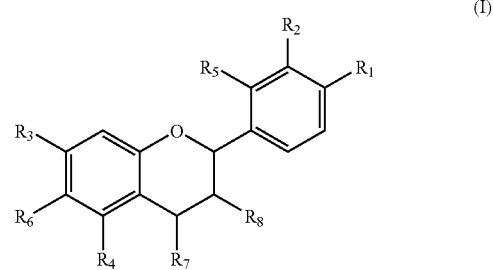

and pharmaceutically acceptable salts, stereoisomers, enantiomers, prodrugs and solvates thereof. The compounds are useful as an agent for enhancing the neurite outgrowth and preventing or treating diseases associated with HDAC in particular, tumor or cell proliferative diseases. In particular, the compounds of the invention can be used as agents for anti-neurodegenerative diseases and human spinal muscular atrophy (SMA).

DETAILED DESCRIPTION OF THE INVENTION

Figure 1:
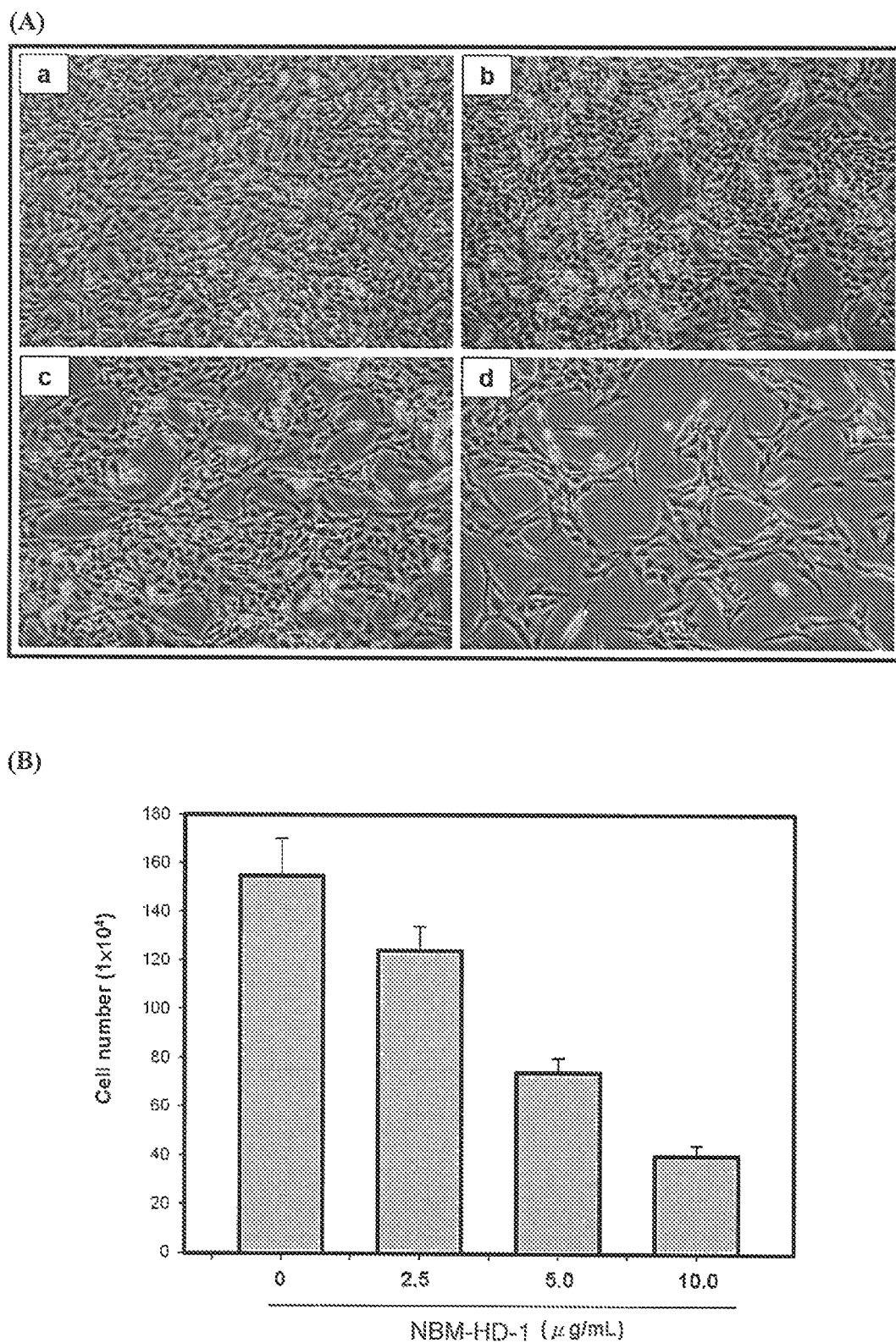
FIG. 1 shows the microscopic photographs of the rat glioma C6 cells treated with different concentrations of NBM-HD-1.

The present invention relates to novel compounds derived from propolins, which are useful as agents for enhancing the neurite outgrowth and preventing and treating of diseases associated with HDAC, in particular, tumor or cell proliferative diseases. The compounds of the invention are potent in inhibiting growth in cancer cells via differentiation pathway. In particular, they can be used as agents for anti-neurodegenerative diseases and human spinal muscular atrophy (SMA).

Compounds of the Invention

Accordingly, the present invention relates to compounds represented by the following formula (I):

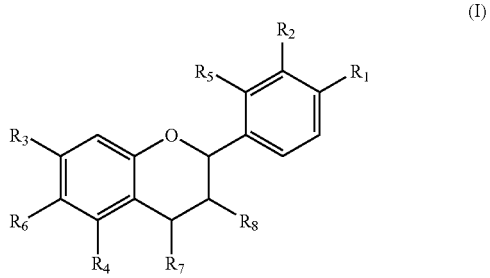

(I)

wherein $R_1$ and $R_2$ are each independently OH, OC(=O)alkyl, O-alkyl, S-alkyl, N-alkyl, O-alkenyl, S-alkenyl, N-alkenyl, O-alkynyl, S-alkynyl, N-alkynyl, O—$C_{3-8}$cycloalkyl, S—$C_{3-8}$cycloalkyl, N—$C_{3-8}$cycloalkyl, O-unsaturated 5- to 10-membered monocyclic or bicyclic ring, S-unsaturated 5- to 10-membered monocyclic or bicyclic ring, N-unsaturated 5- to 10-membered monocyclic or bicyclic ring, alkyl, alkylenyl, alkynyl, $C_{3-8}$cycloalkyl, an unsaturated 5- to 10-membered monocyclic or bicyclic ring or a saturated or unsaturated 5- to 10-membered heterocyclic ring comprising at least one ring heteroatom selected from the group consisting of: N, O and S; or $R_1$ and $R_2$ can together form dioxolane;

$R_3$ and $R_4$ are each independently OH, OC(=O)alkyl, O-alkyl, S-alkyl, N-alkyl, O-alkenyl, S-alkenyl, N-alkenyl, O-alkynyl, S-alkynyl, N-alkynyl, O—$C_{3-8}$cycloalkyl, S—$C_{3-8}$cycloalkyl, N—$C_{3-8}$cycloalkyl, O-unsaturated 5- to 10-membered monocyclic or bicyclic ring, S-unsaturated 5- to 10-membered monocyclic or bicyclic ring, N-unsaturated 5- to 10-membered monocyclic or bicyclic ring, alkyl, alkylenyl, alkynyl, $C_{3-8}$cycloalkyl, an unsaturated 5- to 10-membered monocyclic or bicyclic ring or a saturated or unsaturated 5- to 10-membered heterocyclic ring comprising at least one ring heteroatom selected from the group consisting of: N, O and S;

$R_5$ is $C_{4-16}$ alkyl or $C_{4-16}$alkenyl wherein the alkyl or alkenyl is unsubstituted or substituted with one or more $C_{1-6}$ alkyl, OH, halogen, CN, NO, $N_3$, $NH_2$, CHO, $OR_9$, $SR_9$, $NR_9$, or $COOR_9$;

$R_6$ is $C_{2-12}$ alkyl or $C_{2-12}$ alkenyl wherein the alkyl or alkenyl is unsubstituted or substituted with one or more $C_{1-6}$alkyl, OH, halogen, CN, NO, $N_3$, $NH_2$, CHO, $OR_9$, $SR_9$, or $NR_9$; or one of $R_5$ and $R_6$ is hydrogen, halogen or OH, while the other is $C_{4-16}$ alkyl or $C_{4-16}$alkylene unsubstituted or substituted with one or more $C_{1-6}$alkyl, OH, $NH_2$, halogen, CN, NO or $N_3$;

$R_7$ and $R_8$ are each independently hydrogen, halogen, OH, $NH_2$, COOH, CHO, CN, NO, $C_{1-6}$alkyl unsubstituted or substituted with OH, $NH_2$, COOH, halogen, CN, NO or CHO, =O, O-alkyl, S-alkyl, N-alkyl, O-alkenyl, S-alkenyl, N-alkenyl, O-alkynyl, S-alkynyl or N-alkynyl, or $R_7$ and $R_8$ may together form a double bond, a $C_{3-6}$cycloalkyl, or a 5- to 10-membered heterocyclic ring comprising at least a heteroatom selected from the group consisting of N, O and S;

$R_9$ is phenyl, C(=O)$R^{10}$, C(=O)O$R^{10}$ or benzyl; and $R^{10}$ is OH, NHOH, $NH_2$, $C_{1-6}$alkyl, phenyl or benzyl;

provided that when $R_1$, $R_2$, $R_3$ and $R_4$ are OH, $R_5$ is not

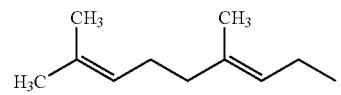

and $R_6$ is not

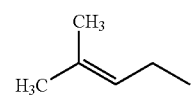

or H; or when $R_1$, $R_2$, $R_3$ and $R_4$ are OH and $R_5$ is H, $R_6$ is not

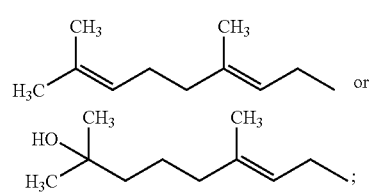

and pharmaceutically acceptable salts, stereoisomers, enantiomers, prodrugs and solvates thereof.

In the context of the present specification, the term "alkyl" means straight or branched hydrocarbon chains. The alkyl is preferably C$_{1-10}$ alkyl. Preferably, the carbon number of alkyl is selected from the group consisting of 1 to 8; more preferably, it is C$_{1-6}$ alkyl or C$_{1-4}$ alkyl. Examples of alkyl groups include methyl (—CH$_3$), ethyl (—CH$_2$CH$_3$), propyl (—CH$_2$CH$_2$CH$_3$), isopropyl (CH$_3$)$_2$CH and butyl (—C$_4$H$_9$).

In the context of the present specification, the term "alkenyl" means both straight and branched chain unsaturated hydrocarbon groups, wherein the unsaturation is present only as double bonds. According to the invention, the alkenyl includes one or more double bonds. The alkenyl is preferably C$_{2-16}$ alkenyl. More preferably, the carbon number of alkenyl is selected from the group consisting of 2 to 12. Examples of alkenyl groups include ethenyl (—CH═CH$_2$), propenyl (—CH═CHCH$_3$ or —CH$_2$CH═CH$_2$), butenyl (—CH$_2$CH═CHCH$_3$ or —CH═CHCH$_2$CH$_3$ or —CH$_2$CH$_2$CH═CH$_2$), —CH$_2$CH═C(CH$_3$)CH$_3$, —CH$_2$—CH═CH—CH$_2$—CH$_2$—CH═CH—CH$_3$ and —CH$_2$—CH═C(CH$_3$)—CH$_2$—CH$_2$—CH═C(CH$_3$)—CH$_3$.

In the context of the present specification, the term "alkynyl" means both straight and branched chain unsaturated hydrocarbon groups, wherein the unsaturation is present only as triple bonds. Preferably, the carbon number of alkynyl is selected from the group consisting of 2 to 8. More preferably, alkynyl is C2-6 alkynyl or C2-4 alkynyl. Examples of alkynyl groups include propynyl (e.g., —CH$_2$C≡CH).

In the context of the present specification, the term "cycloalkyl" means an aliphatic ring (saturated carbocyclic ring). Preferably, the carbon number of cycloalkyl is selected from the group consisting of 3 to 8. Examples of cycloalkyl groups include cyclopropyl, cyclobutyl, cyclopentyl and cyclohexyl.

In the context of the present specification, the term "unsaturated 5- to 10-membered monocyclic or bicyclic ring" means unsaturated 5- to 10-membered monocyclic or bicyclic (fused or otherwise) ring system, examples of which include phenyl and naphthyl.

In the context of the present specification, the term "saturated or unsaturated 5- to 10-membered heterocyclic ring comprising at least one ring heteroatom selected from the group consisting of: N, O and S" means a saturated or unsaturated 5- to 10-membered heterocyclic ring system comprising at least one ring heteroatom selected from nitrogen, oxygen and sulphur, each group being optionally substituted by at least one substituent selected from nitro, hydroxyl, oxo, halogen, carboxyl, C$_1$-C$_6$alkyl, C$_1$-C$_6$alkoxy, C$_1$-C$_6$alkylthio, C$_1$-C$_6$alkylcarbonyl, C$_1$-C$_6$ alkoxycarbonyl and phenyl. Examples of the heterocyclic ring includes pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, and the like.

In the context of the present specification, the term "halogen" means fluorine, chlorine, bromine and iodine.

In the context of the present specification, the term "pharmaceutically acceptable salt" includes those formed with both organic and inorganic acids and bases. Pharmaceutically acceptable acid addition salts include those formed from mineral acids such as: hydrochloric, hydrobromic, sulphuric, and phosphoric, acid; and organic acids such as: citric, tartaric, lactic, pyruvic, acetic, trifluoroacetic, succinic, oxalic, formic, fumaric, maleic, oxaloacetic, methanesulphonic, ethanesulphonic, p-toluenesulphonic, benzenesulphonic and isethionic acids. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines.

In the context of the present specification, the term "prodrug" means a compound which is converted within the body, e.g., by hydrolysis in the blood, into its active form that has medical effects.

In the context of the present specification, the term "solvate" means a complex comprising the compound of the invention and a solvent in which they are reacted or from which they are precipitated or crystallized.

In the context of the present specification, the term "stereoisomers" are isomeric molecules whose atomic connectivity is the same but whose atomic arrangement in space is different.

In the context of the present specification, the term "enantiomers" are stereoisomers that are nonsuperimposable complete mirror images of each other, much as one's left and right hands are "the same" but opposite.

According to one embodiment of the compounds of formula (I) of the invention, preferably, R$_1$ and R$_2$ are each independently OH, OC$_{1-6}$alkyl, OC(═O)C$_{1-6}$alkyl, O-phenyl or O-benzyl or R$_1$ and R$_2$ together form dioxolane. More preferably, R$_1$ and R$_2$ are each independently OH, OCH$_3$, OCH$_2$CH$_3$, OCH$_2$CH$_2$CH$_3$, OC(═O)CH$_3$, O-phenyl or O-benzyl.

According to one embodiment of the compounds of formula (I) of the invention, preferably, R$_3$ and R$_4$ are each independently OH, OC$_{1-6}$alkyl, OC(═O)C$_{1-6}$alkyl, O-phenyl or O-benzyl. More preferably, R$_3$ and R$_4$ are each independently OH, OCH$_3$, OCH$_2$CH$_3$, OCH$_2$CH$_2$CH$_3$, OC(═O)CH$_3$, O-phenyl or O-benzyl.

According to one embodiment of the compounds of formula (I) of the invention, preferably, R$_5$ is

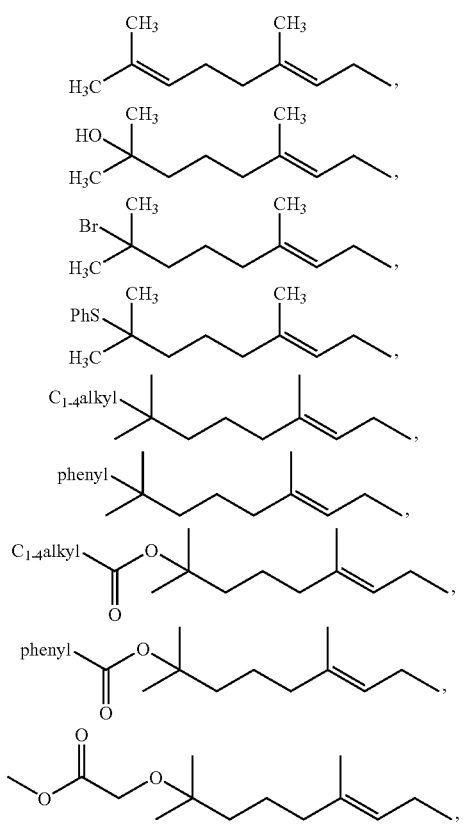

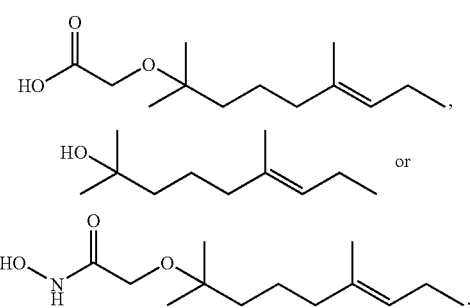
According to one embodiment of the compounds of formula (I) of the invention, preferably, $R_6$ is
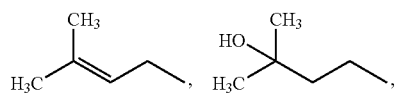
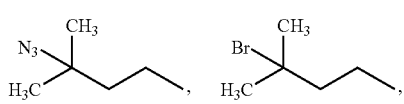
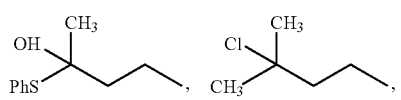
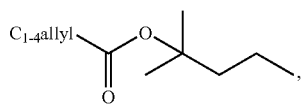
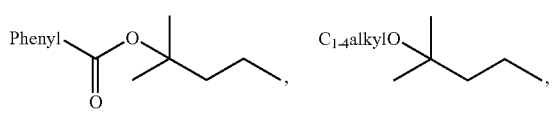
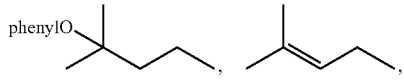
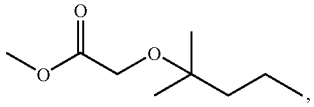
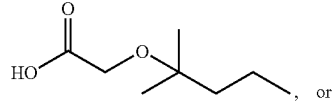
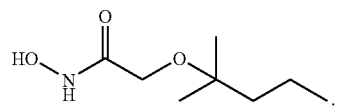
According to the invention, the preferred compound of formula (I) of the invention is selected from the group consisting of:
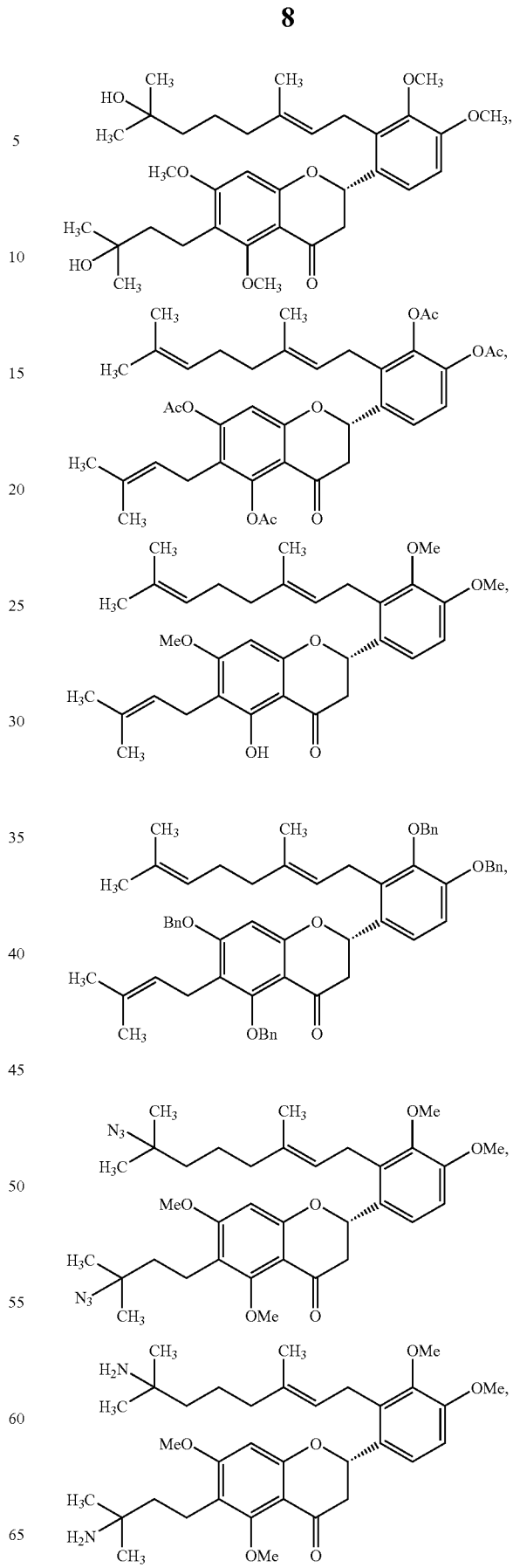

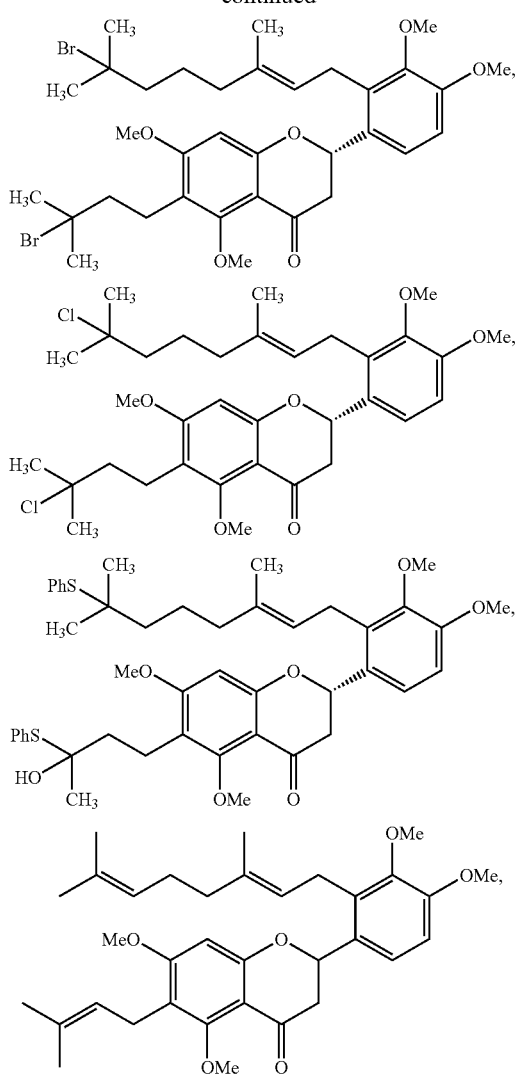
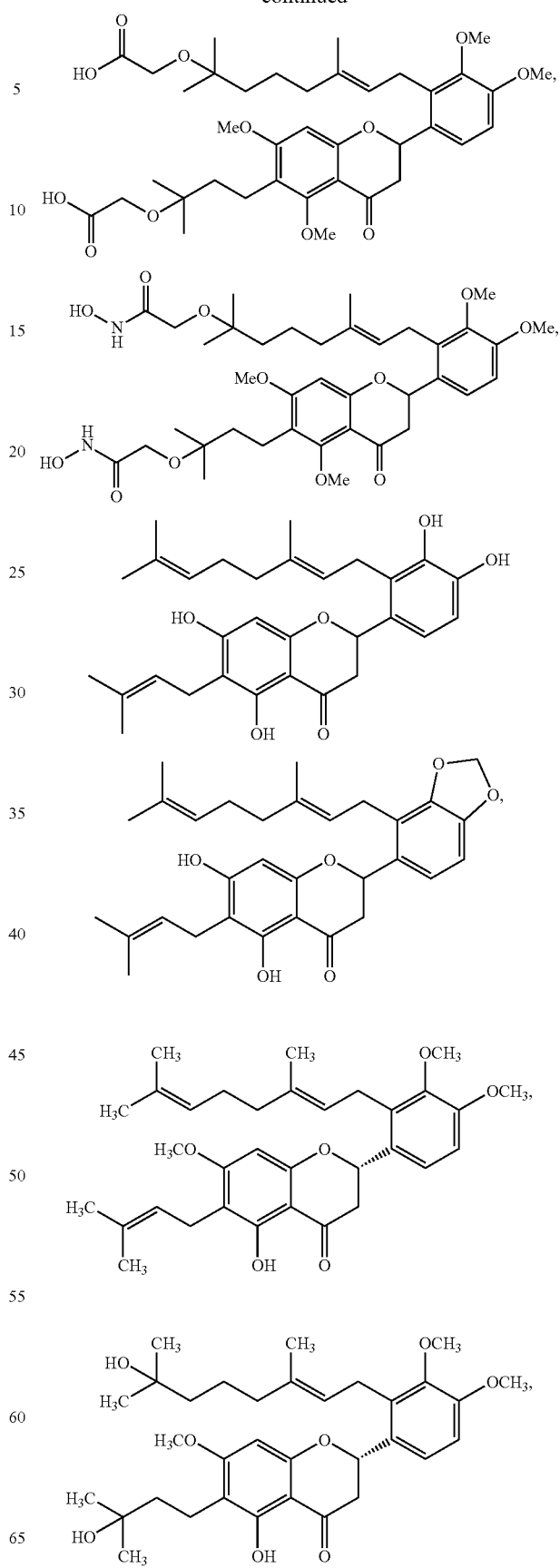

-continued

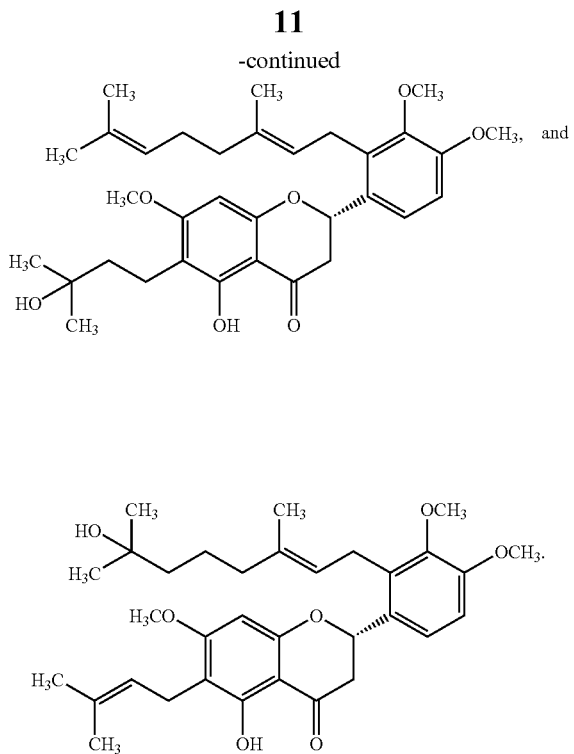

and

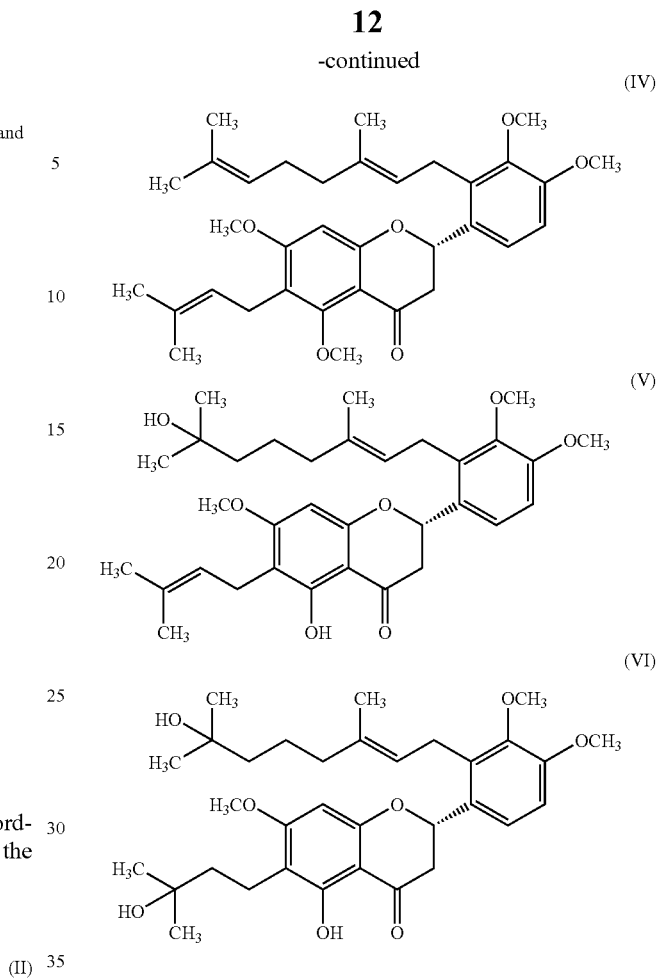

The present invention also relates to a stereoisomer according to the compound of formula (I), and is represented by the following formula (II):

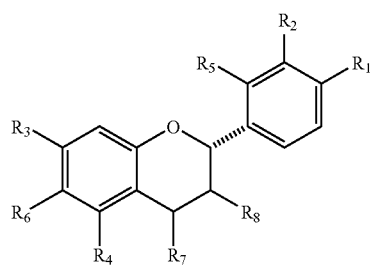
(II)

wherein $R_1$, $R_2$, $R_3$, $R_4$, $R_5$, $R_6$, $R_7$ and $R_8$ are defined as those in formula (I).

According to a more preferred embodiment of the invention, the compound of formula (I) is that having the following formula (III), (IV), (V) or (VI):

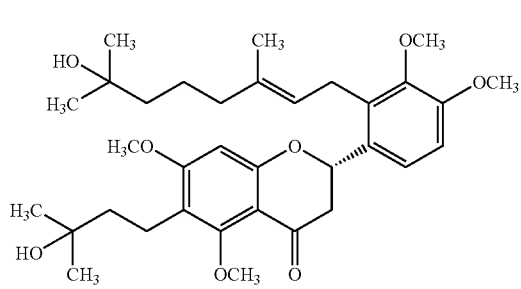
(III)

According to the invention, the compounds of formula (I) of the invention can inhibit HDAC and thus can be used as agents for prevention or treatment of diseases associated with histone deacetylase (HDAC). In addition, the compounds of the invention significantly inhibit growth of multiple cancer cell lines, including those of rat C6 glioma, human glioblastoma, human breast cancer cells, human leukemia cells, and human melanoma cells. The mechanism for inhibiting the growth of cancer cells may be via differentiation pathway, in particular via induced differentiation and regulated cell cycle regulator gene expression, including those of p21 and cyclin B1. In addition, the compounds of formula (I) of the invention can mediate neuronal differentiation of neural stem cells and thus can be used as agents against anti-neurodegenerative diseases.

For the therapeutic uses of the compounds of the invention, the dosage administered will, of course, vary with the compound employed, the mode of administration, the treatment desired and the disorder indicated. The daily dosage of the compound of formula (I) may be in the range from 1 mg/kg to 40 mg/kg. The invention provides the methods of inhibiting HDAC, treating tumor or cell proliferative disease, neurodegenerative diseases and human spinal muscular atrophy and enhancing the neurite outgrowth in a subject, comprising administrating to the subject a therapeutically effective amount of the compounds of the invention, respectively.

General Synthesis of the Compounds of Formula I of the Invention

The compounds of the present invention can be prepared by any conventional means. Suitable processes for synthesizing these compounds are provided in the examples. Generally, compounds of formula I can be prepared according to one of the described synthetic schemes below:
Scheme 1
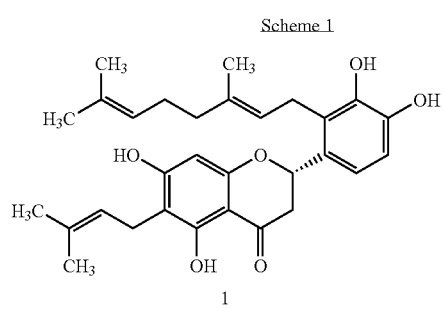
1
K₂CO₃, DMS
acetone, Δ →
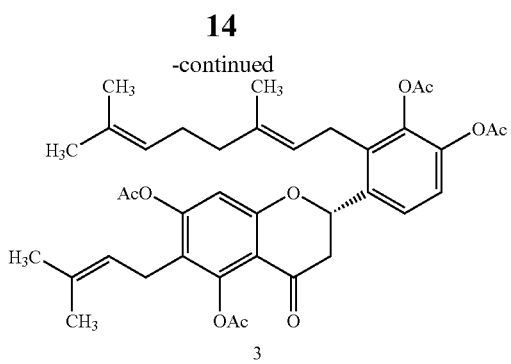
3
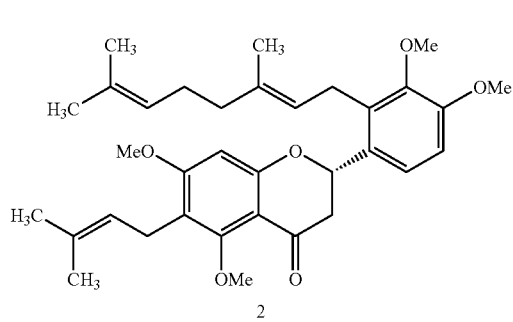
2
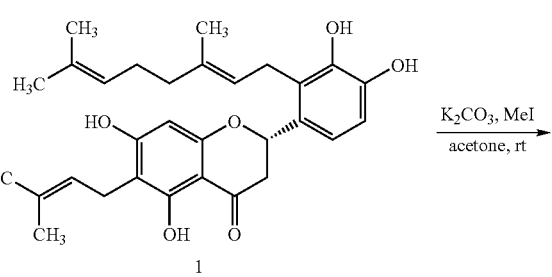
1
K₂CO₃, MeI
acetone, rt →
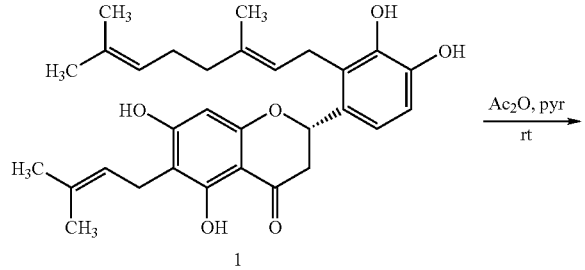
1
Ac₂O, pyr
rt →
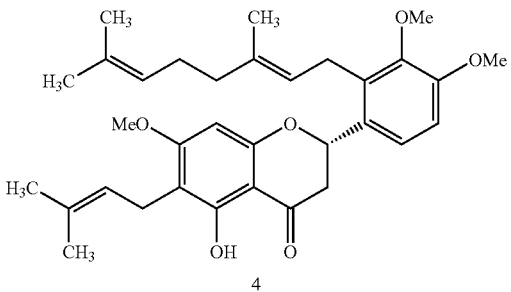
4
Scheme 2
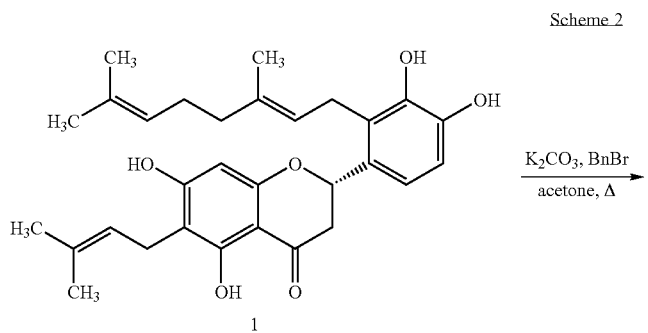
1
K₂CO₃, BnBr
acetone, Δ →
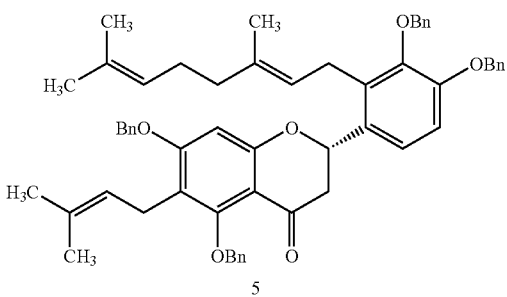
5

15

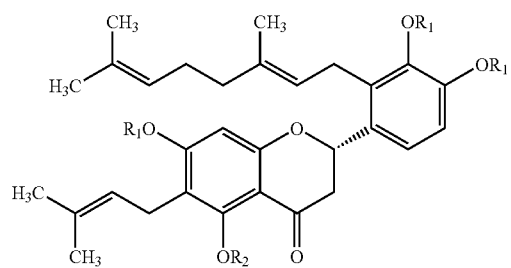

1: R₁ = R₂ = H
2: R₁ = R₂ = Me
3: R₁ = R₂ = Ac
4: R₁ = Me, R₂ = H
5: R₁ = R₂ = Bn

H₂SO₄-THF, rt

16

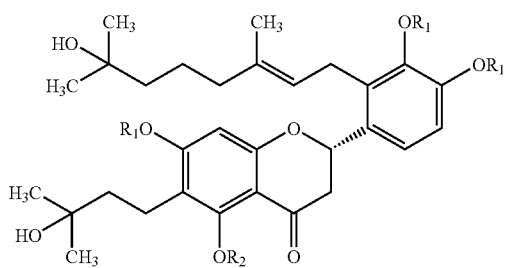

6a: R₁ = R₂ = H
6b: R₁ = R₂ = Me
6c: R₁ = R₂ = Ac
6d: R₁ = Me, R₂ = H
6e: R₁ = R₂ = Bn

PhI(OAc)₂, MeCN, Δ

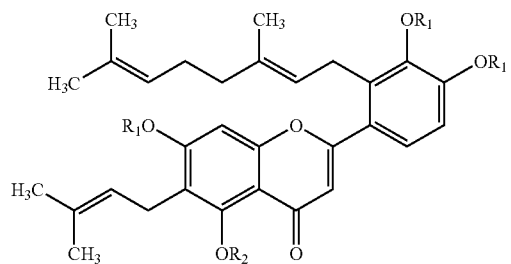

1: R₁ = R₂ = H
2: R₁ = R₂ = Me
3: R₁ = R₂ = Ac
4: R₁ = Me, R₂ = H
5: R₁ = R₂ = Bn

H₂SO₄-THF, rt

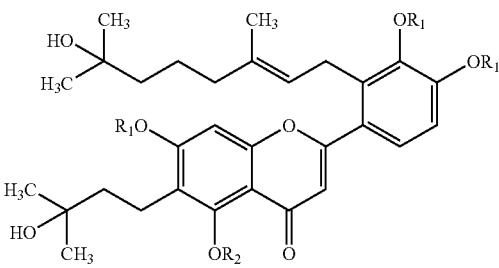

7a: R₁ = R₂ = H
7b: R₁ = R₂ = Me
7c: R₁ = R₂ = Ac
7d: R₁ = Me, R₂ = H
7e: R₁ = R₂ = Bn

Scheme 3

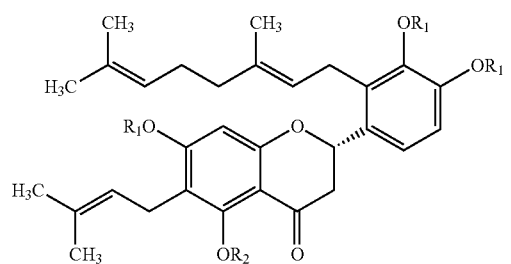

1: R₁ = R₂ = H
2: R₁ = R₂ = Me
3: R₁ = R₂ = Ac
4: R₁ = Me, R₂ = H
5: R₁ = R₂ = Bn

NaBH₄, MeOH, rt

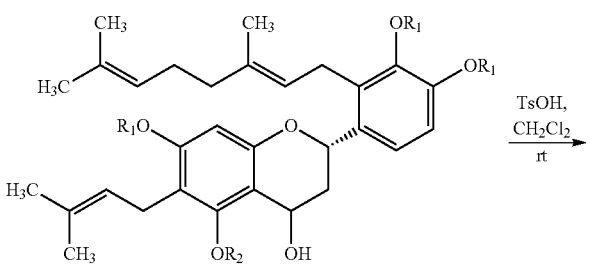

8a: R₁ = R₂ = H
8b: R₁ = R₂ = Me
8c: R₁ = R₂ = Ac
8d: R₁ = Me, R₂ = H
8e: R₁ = R₂ = Bn

TsOH, CH₂Cl₂, rt

17
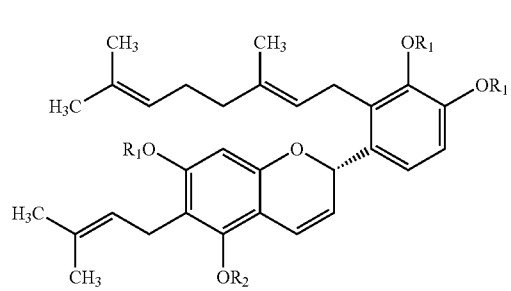
18
-continued
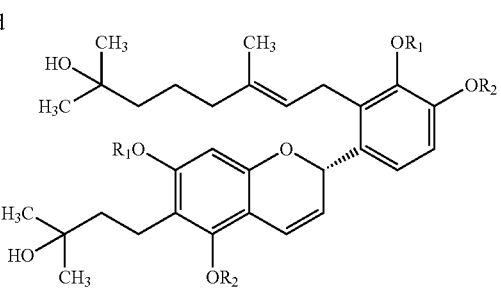
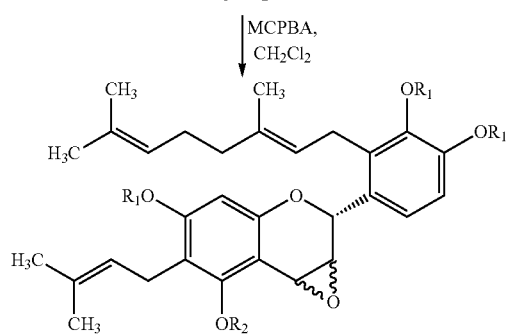
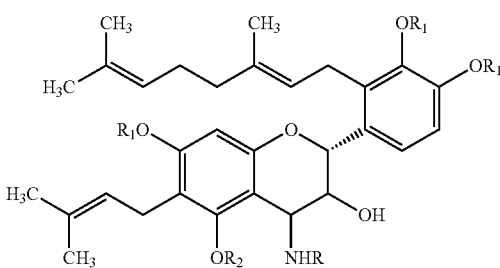
Scheme 4
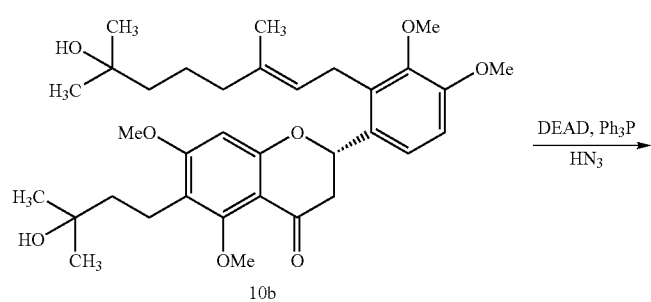
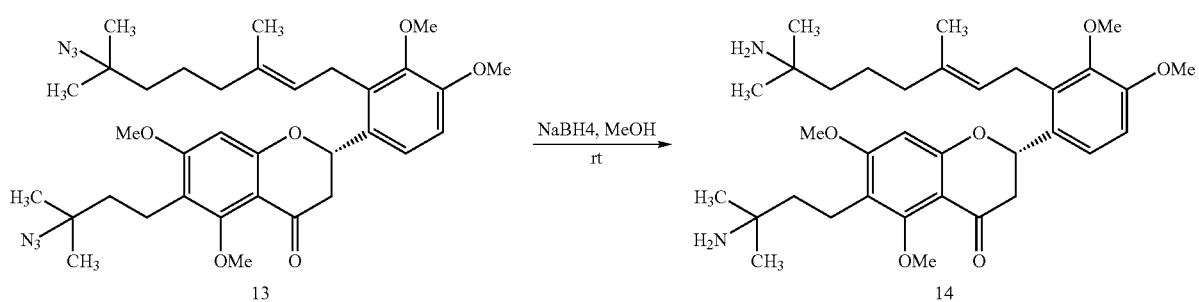

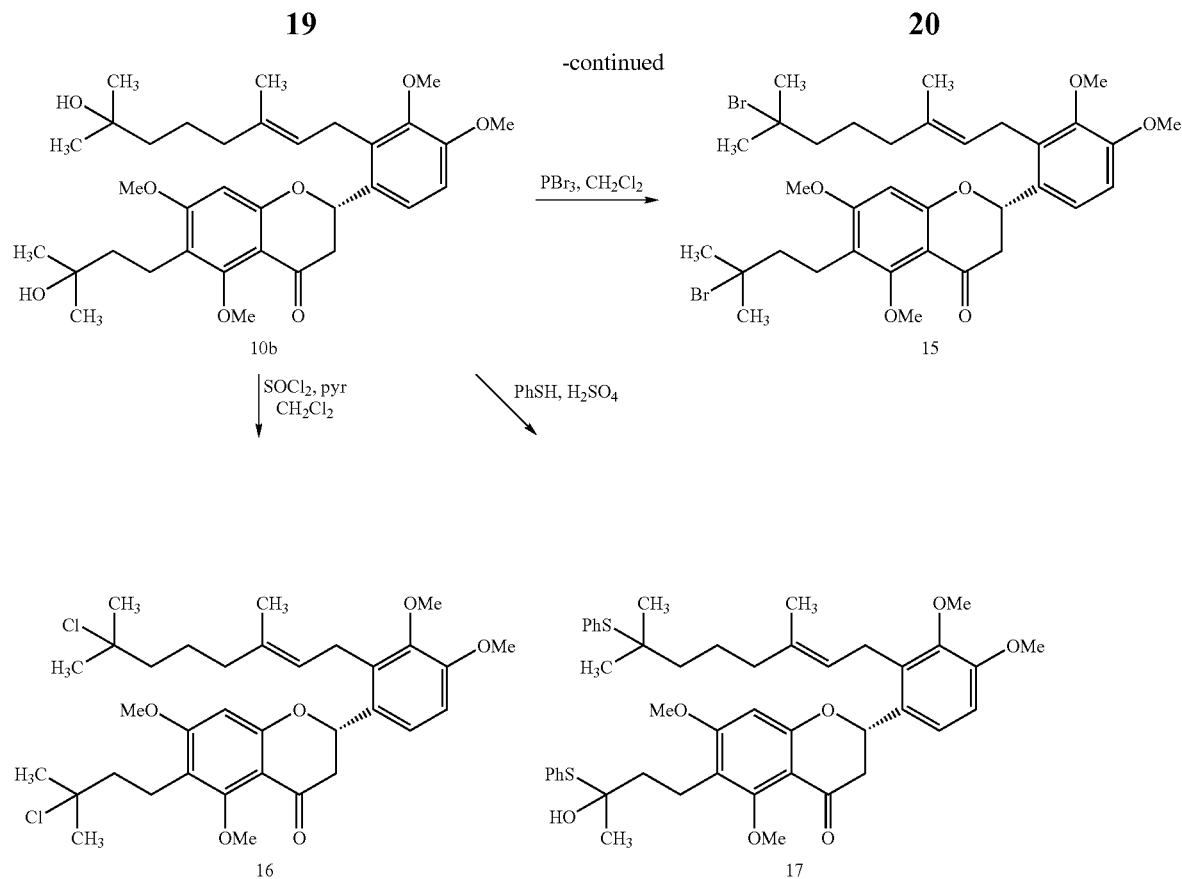
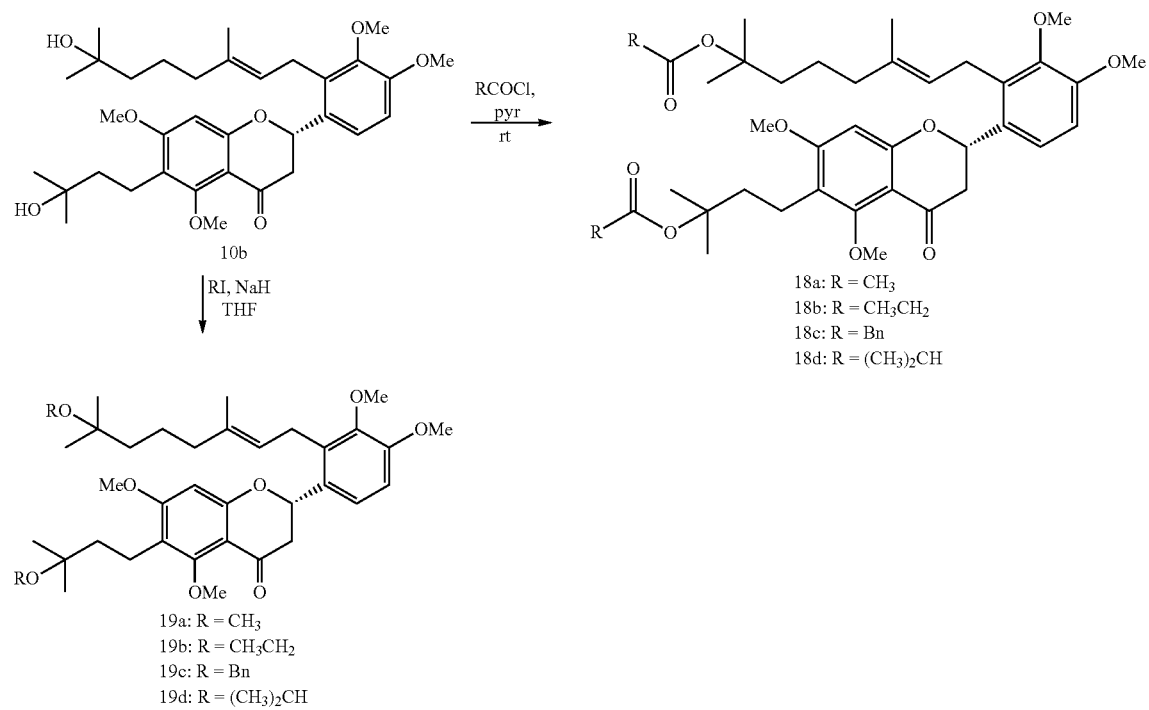

Scheme 6
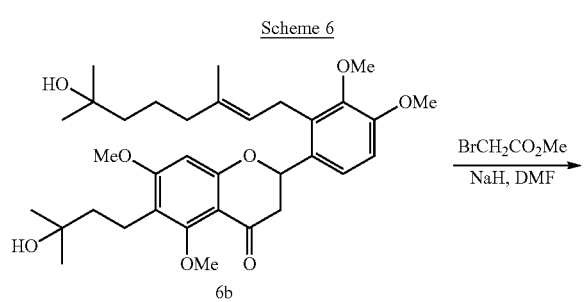
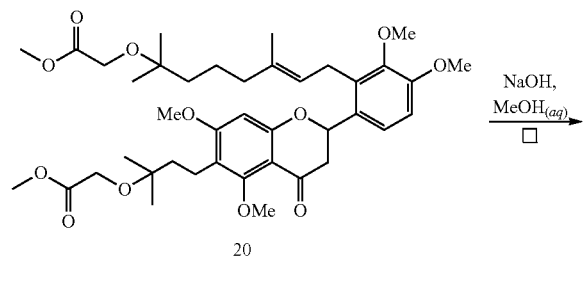
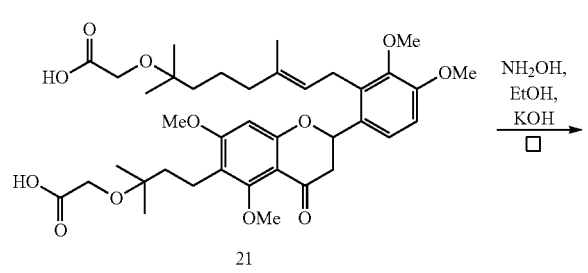
Scheme 7
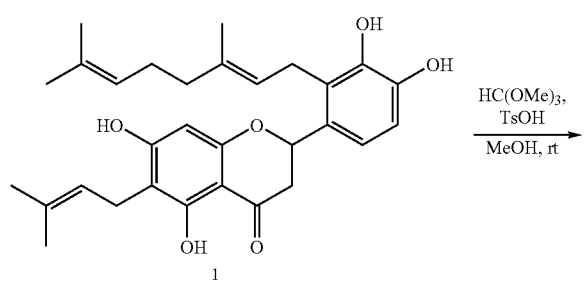
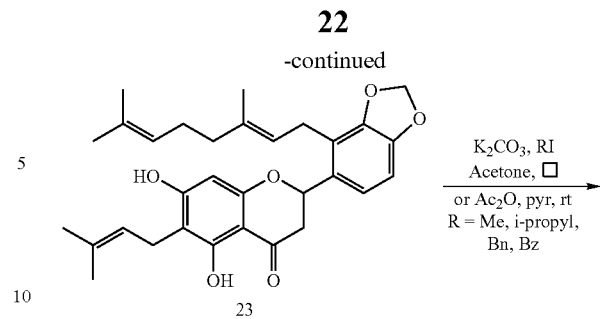
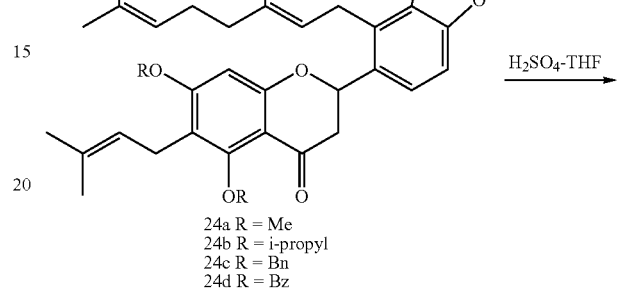
24a R = Me
24b R = i-propyl
24c R = Bn
24d R = Bz
24e R = Ac
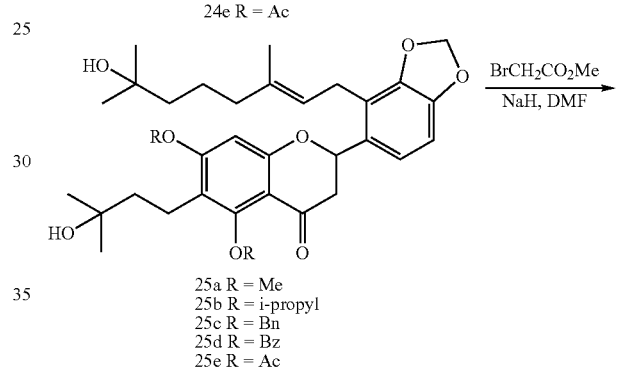
25a R = Me
25b R = i-propyl
25c R = Bn
25d R = Bz
25e R = Ac
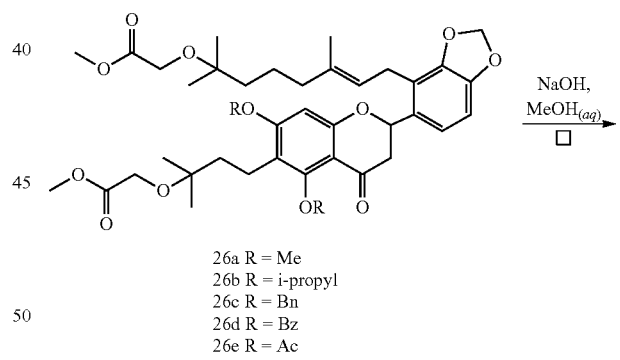
26a R = Me
26b R = i-propyl
26c R = Bn
26d R = Bz
26e R = Ac
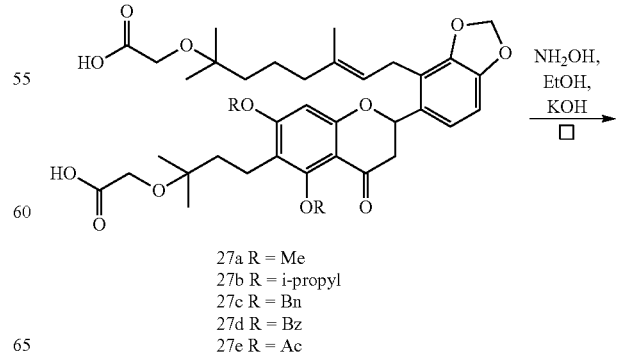
27a R = Me
27b R = i-propyl
27c R = Bn
27d R = Bz
27e R = Ac

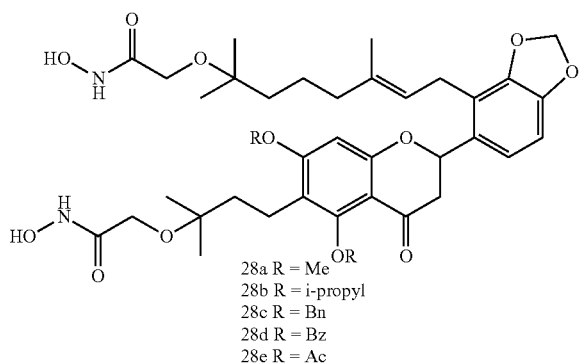

Scheme 8

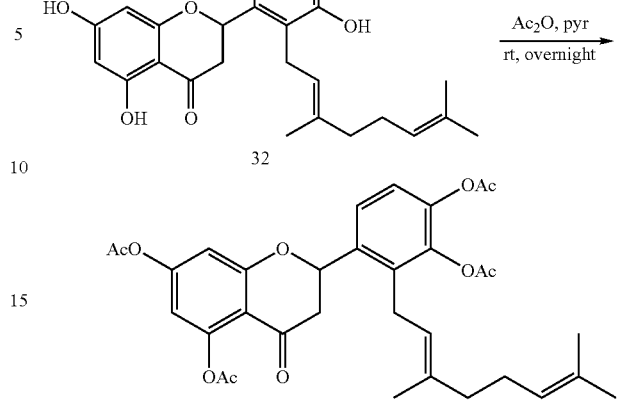

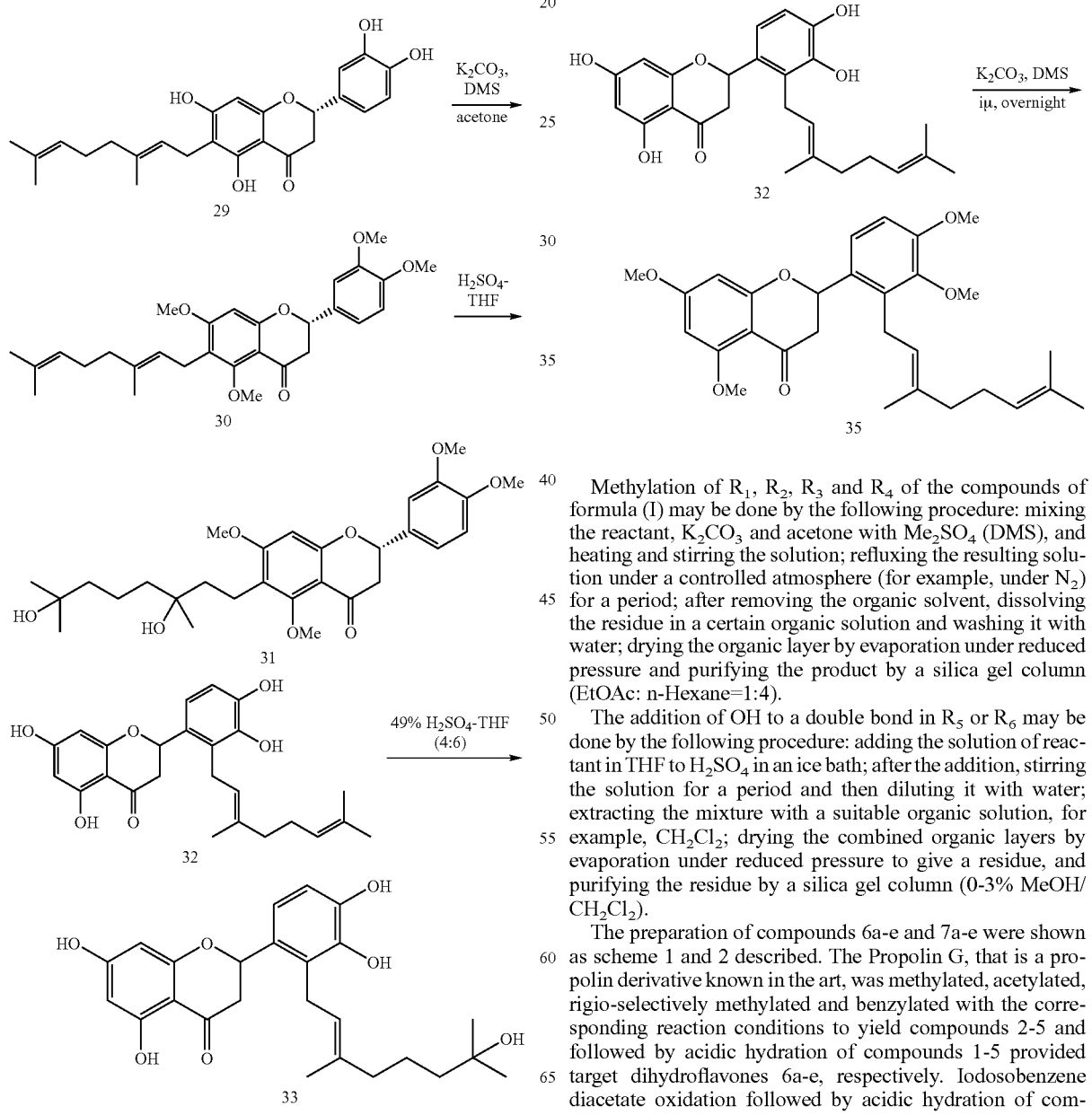

Methylation of $R_1$, $R_2$, $R_3$ and $R_4$ of the compounds of formula (I) may be done by the following procedure: mixing the reactant, $K_2CO_3$ and acetone with $Me_2SO_4$ (DMS), and heating and stirring the solution; refluxing the resulting solution under a controlled atmosphere (for example, under $N_2$) for a period; after removing the organic solvent, dissolving the residue in a certain organic solution and washing it with water; drying the organic layer by evaporation under reduced pressure and purifying the product by a silica gel column (EtOAc: n-Hexane=1:4).

The addition of OH to a double bond in $R_5$ or $R_6$ may be done by the following procedure: adding the solution of reactant in THF to $H_2SO_4$ in an ice bath; after the addition, stirring the solution for a period and then diluting it with water; extracting the mixture with a suitable organic solution, for example, $CH_2Cl_2$; drying the combined organic layers by evaporation under reduced pressure to give a residue, and purifying the residue by a silica gel column (0-3% MeOH/$CH_2Cl_2$).

The preparation of compounds 6a-e and 7a-e were shown as scheme 1 and 2 described. The Propolin G, that is a propolin derivative known in the art, was methylated, acetylated, rigio-selectively methylated and benzylated with the corresponding reaction conditions to yield compounds 2-5 and followed by acidic hydration of compounds 1-5 provided target dihydroflavones 6a-e, respectively. Iodosobenzene diacetate oxidation followed by acidic hydration of compounds 1-5 afforded the corresponding flavones 7a-e.

Compounds 10a-e and 12a-e were prepared as outlined in scheme 3. Sodium borohydride reduction followed by dehydration of compounds 1-5 gave the corresponding compounds 9a-e. Acidic hydration of 9a-e yielded target compounds 10a-e, respectively. MCPBA epoxidation of compounds 9a-e provided the epoxides 11a-e, and the ensuing nucleophilic reaction with corresponding amines such as methylamine, ethylamine and enzylamine afforded target compounds 12a-e, respectively.

Compounds 14-17 were synthesized as scheme 4 described. Mitsunobu reaction of 10b gave desired azide 13 and the ensuing sodium reaction converted azide to tertiary amine 14. Bromination with phorsphorus tribromide, thiolation with phenol thiol (PhSH) and chlorination with thionyl chloride of compound 10b provided bromide 15, thiol ether 17 and chloride 16, respectively.

Compounds 18a-d and 19a-d were prepared as scheme 5 described. Acylation of compound 10b with corresponding acyl chlorides such as acetyl, propionyl, benzoyl and isobutyryl gave compounds 18a-d, respectively. Alkylation of compound 10b with corresponding alkyl iodides such as methyl, ethyl, benzyl and isopropyl iodide afforded compounds 19a-d, respectively.

Compound 22 was synthesized as scheme 6 showed. Reaction of tertiary alcohol of compound 6b with ethyl bromoacetate under sodium hydride condition gave compound 20. Basic hydrolysis of compound 20 afforded compound 21 and following reaction with hydroxylamine yielded hydroxamic acid 22.

Hydroxyamic acids 28a-e were prepared as scheme 7 described. Reaction of compound 1 with trimethyl orthoformate under acidic conditions gave acetonide 23 and the ensuing alkylation with alkyl iodides such as methyl, isopropyl and benzyl, or acylation with benzoyl chloride and acetic anhydride afforded compounds 24a-e, respectively. Acidic hydration of two terminal olefins of compounds 24a-e provided compounds 25a-e and the ensuing reaction with ethyl bromoacetate gave compounds 26a-e. Basic hydrolysis of compounds 26a-e afforded compounds 27a-e and the ensuing reaction with hydroxylamine yielded hydroxamic acids 28a-e, respectively.

Pharmaceutical Composition of the Invention

The compounds of formula (I) and pharmaceutically acceptable salts, stereoisomers, enantiomers, prodrugs and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 10 to 30 wt % (percent by weight), more preferably from 30 to 50 wt %, still more preferably from 50 to 70 wt %, and even more preferably from 70 to 100 wt %, of the active ingredient, all percentages by weight being based on total composition. In addition, the pharmaceutical composition of the invention may further comprise other agents for prevention or treatment of diseases associated with histone deacetylase (HDAC).

The pharmaceutical compositions may be administered systemically, e.g., by oral administration in the form of tablets, capsules, syrups, powders or granules; or by parenteral administration in the form of solutions or suspensions; or by subcutaneous administration; or by rectal administration in the form of suppositories; or transdermally.

The compounds and pharmaceutical compositions of the invention are an HDAC inhibitor and can be retained long in the cells and continuously induce the acetylation of histone H4. They are HDAC inhibitors inducing differentiation of cells and neural stem cells. In addition, the compounds of the invention significantly inhibits HDAC activity. The compounds of the invention significantly decrease both S and G2/M phases of the cells in a dose-dependent manner and change the morphology of cancer cells. Therefore, the compounds of the invention can treat tumor or cell proliferative disease. Moreover, the compounds of the invention can enhance the neurite outgrowth and treat neurodegenerative diseases and human spinal muscular atrophy (SMA).

EXAMPLE

The following examples illustrate preferred methods for synthesizing and using the compounds:

Example 1

Preparation of 3',4',5,7-Tetramethyl-propolin G (2)

To the mixture of Propolin G (1, 5 g, 10.16 mmol), $K_2CO_3$ (16.27 g, 117.89 mmol) and acetone (280 mL) $Me_2SO_4$ (15.76 mL, 126 mmol) was added and the resulting solution was heated to reflux under nitrogen for 24 h. After removal of the organic solvent, the residue was dissolved in $CH_2Cl_2$ (80 mL) and washed with $H_2O$ (40 mL×3). The $CH_2Cl_2$ layers were dried over $Na_2SO_4$ and evaporated under reduced pressure. The residue obtained was purified by a silica gel column (EtOAc: n-Hexane=1:6) to give compound 2 (4.00 g, 72%): $^1$H-NMR (400 MHz, $CDCl_3$) □ 7.26 (1H, d, J=8.6 Hz), 6.86 (1H, d, J=8.6 Hz), 6.27 (1H, s), 5.50 (1H, dd, J=2.5, 13.5 Hz), 5.14-5.11 (1H, m), 5.11-5.10 (1H, m), 5.02-4.99 (1H, m), 3.87 (3H, s), 3.83 (3H, s), 3.79 (6H, s), 3.50 (1H, dd, J=6.6, 15.2 Hz), 3.43 (1H, dd, J=5.8, 15.2 Hz), 3.00 (1H, dd, J=13.5, 16.7 Hz), 2.68 (1H, dd, J=2.6, 16.7 Hz), 2.00-1.92 (2H, m), 1.75 (3H, s), 1.70 (3H, s), 1.65 (3H, s), 1.60 (3H, s), 1.52 (3H, s); $^{13}$C-NMR (100 MHz, $CDCl_3$) □ 189.4 (s), 164.0 (s), 163.3 (s), 159.6 (s), 153.0 (s), 147.2 (s), 135.6 (s), 134.2 (s), 131.5 (s), 131.3 (s), 129.8 (s), 124.1 (d), 122.8 (d), 122.7 (d), 122.1 (d), 118.2 (s), 110.3 (d), 108.7 (s), 95.6 (d), 75.9 (d), 61.8 (q), 60.7 (q), 55.7 (q), 55.7 (q), 45.1 (t), 39.6 (t), 26.6 (t), 25.7 (q), 25.6 (q), 24.9 (t), 22.0 (t), 17.7 (q), 17.6 (q), 16.3 (q); HRE-IMS Calcd for $C_{34}H_{44}O_6$ (M) 548.3142, Found 548.3140.

Example 2

Preparation of 6-(2-Hydroxy-2-methylbutyl)-2'-(7-hydroxy-3,7-dimethyloct-2-enyl)-3',4',5,7-tetramethoxyflavanone (6b)

To a solution of compound 2 (7 g, 12.77 mmol) in THF (170 mL) 49% $H_2SO_4$ (140 mL) was added in an ice bath. After complete addition, the reaction mixture was stirred at rt for 8 h and then diluted with $H_2O$. The reaction mixture was extracted with $CH_2Cl_2$ (100 mL×3). The combined organic layers were dried over $Na_2SO_4$ and evaporated under reduced pressure to give a residue, which was purified by a silica gel column (n-hexane:EtOAc=1:1~1:3) to give pure oil 6b (2.30 g, 34%). $^1$H-NMR (400 MHz, $CDCl_3$) □ 7.27 (1H, d, J=8.6 Hz), 6.87 (1H, d, J=8.6 Hz), 6.28 (1H, d, J=2.6 Hz), 5.49 (1H, dd, J=2.4, 13.6 Hz), 5.05 (1H, t, J=6.0 Hz), 3.87 (3H, s), 3.84 (3H, s), 3.79 (6H, s), 3.52 (1H, dd, J=5.5, 15.2 Hz), 3.43 (1H, dd, J=7.6, 15.2 Hz), 2.97 (1H, dd, J=8.0, 16.7 Hz), 2.70-2.59 (3H, m), 1.93 92H, t, J=6.4 Hz), 1.65 (3H, s), 1.64-1.60 (2H, m), 1.41-1.32 (4H, m), 1.25 (6H, s), 1.15 (3H, s), 1.14 (3H, s); $^{13}$C-NMR (100 MHz, $CDCl_3$) 189.4 (s), 164.0 (s), 163.3 (s), 159.6 (s), 153.0 (s), 147.2 (s), 135.6 (s), 134.2 (s), 131.5 (s), 131.3 (s), 129.8 (s), 124.1 (d), 122.8 (d), 122.7 (d), 122.1 (d), 118.2 (s), 110.3 (d), 108.7 (s), 95.6 (d), 75.9 (d), 61.8 (q), 60.7 (q), 55.7 (q), 55.7 (q), 45.1 (t), 39.6 (t), 26.6 (t), 25.7 (q), 25.6 (q), 24.9 (t), 22.0 (t), 17.7 (q), 17.6 (q), 16.3 (q); HREIMS Calcd for $C_{34}H_{48}O_8$ (M) 584.3338, Found 584.3344.

Example 3

Preparation of 6-Geranyl-3',4',5,7-tetramethoxyflavanone (30)

To the mixture 29 (Propolin C, 128 mg, 0.31 mmol), $K_2CO_3$ (431 mg, 3.1 mmol) and acetone (15 mL) was added $Me_2SO_4$ (0.25 mL, 2.48 mmol) and the resulting solution was heated to reflux under nitrogen for 24 h. After removal of the organic solvent, the residue was dissolved in $CH_2Cl_2$ (50 mL) and washed with $H_2O$ (50 mL×3). The organic layer was dried over $Na_2SO_4$ and evaporated under reduced pressure. The residue obtained was purified by a silica gel column (EtOAc: n-Hexane=1:4) to give compound 33 (107 mg, 72%). $^1$H-NMR (400 MHz, $CDCl_3$) 6.99-6.97 (2H, m), 6.88 (1H, d, J=8.8 Hz), 6.31 (1H, s), 5.33 (1H, dd, J=2.8, 13.3 Hz), 5.11 (1H, td, J=1, 6.9 Hz), 5.04 (1H, td, J=1.3, 5.5 Hz), 3.90 (3H, s, OMe), 3.88 (3H, s, OMe), 3.81 (3H, s, OMe), 3.80 (3H, s, OMe), 3.34 (1H, dd, J=7.2, 14.1 Hz), 3.26 (1H, dd, J=7.2, 14.1 Hz), 3.02 (1H, dd, J=13.3, 16.7 Hz), 2.74 (1H, dd, J=2.8, 16.7 Hz), 2.04-2.00 (2H, m), 1.96-1.92 (2H, m), 1.74 (3H, s), 1.62 (3H, s), 1.55 (3H, s); $^{13}$C-NMR (100 MHz, $CDCl_3$) 189.1 (s), 164.1 (s), 163.0 (s), 159.4 (s), 149.5 (s), 149.4 (s), 131.3, 131.2 (s), 124.4 (d), 122.9 (d), 118.9 (d), 109.5 (d), 108.9 (s), 95.7 (d), 79.2 (q), 61.9 (q), 56.1 (q), 56.0 (q), 55.9 (q), 45.6 (t), 39.8 (t), 26.7 (t), 25.7 (s), 22.0 (t), 17.7 (q), 16.1 (q); HREIMS Calcd for $C_{29}H_{36}O_6$ (M) 480.2510, Found 480.2511.

Example 4

Preparation of 6-(2,6-Dihydroxy-2,6-dimethyl-octyl)-3',4',5,7-tetramethoxyflavanone (31)

To a solution of compound 30 (80 mg, 0.17 mmol) in THF (6 mL) 49% $H_2SO_4$ (4 mL) was added in an ice bath. After complete addition, the reaction mixture was stirred at rt for 8 h and then diluted with $H_2O$. The reaction mixture was extracted with $CH_2Cl_2$ (50 mL×3). The combined organic layers were dried over $Na_2SO_4$ and evaporated under reduced pressure to give a residue, which was purified by a silica gel column (0-3% MeOH/$CH_2Cl_2$) to give pure oil 31 (44 mg, 50%). $^1$H-NMR (400 MHz, $CDCl_3$) □6.99-6.97 (2H, m), 6.88 (1H, d, J=8.8 Hz), 6.31 (1H, s), 5.33 (1H, dd, J=2.8, 13.3 Hz), 3.90 (3H, s, OMe), 3.88 (3H, s, OMe), 3.84 (3H, s, OMe), 3.82 (3H, s, OMe), 3.02 (1H, dd, J=13.3, 16 Hz), 2.75 (1H, dd, J=2.8, 16 Hz), 2.62-2.58 (2H, m), 1.63-1.59 (7H, m), 1.49-1.48 (2H, m), 1.23 (3H, s), 1.22 (3H, s), 1.21 (3H, s); $^{13}$C-NMR (100 MHz, $CDCl_3$) 189.1 (s), 164.1 (s), 163.0 (s), 159.4 (s), 149.5 (s), 149.4 (s), 131.2 (s), 119.0 (d), 118.9 (d), 111.3 (d), 109.5 (d), 108.9 (s), 95.8 (d), 72.9 (s), 71.1 (s), 62.1 (q), 56.0 (q), 55.9 (q), 45.5 (t), 44.5 (t), 42.3 (t), 42.1 (t), 41.5 (t), 29.4 (q), 29.3 (q), 26.9 (q), 26.8 (q), 18.8 (t), 17.5 (t); HREIMS Calcd for (M-18) 498.2602, Found 498.2610.

Example 5

Preparation of Porpolin A (33)

To a solution of Propolin D (compound 32, 100 mg, 0.24 mmol) in THF (6 mL) 49% $H_2SO_4$ (4 mL) was added in an ice bath. After complete addition, the reaction mixture was stirred at rt for 8 h and then diluted with $H_2O$. The reaction mixture was extracted with $CH_2Cl_2$ (50 mL×3). The combined organic layers were dried over $Na_2SO_4$ and evaporated under reduced pressure to give a residue, which was purified by a silica gel column (0-3% MeOH/$CH_2Cl_2$) to give pure oil 33 (42 mg, 40%). $^1$H-NMR (400 MHz, MeOD) 6.87 (1H, d, J=8.4 Hz), 6.71 (1H, d, J=8.4 Hz), 5.88 (2H, dd, J=1.9, 3.3 Hz), 5.47 (1H, dd, J=2.6, 13 Hz), 5.12 (1H, dd, J=5.7, 6.7 Hz), 3.47 (2H, d, J=6.6 Hz), 3.10 (1H, dd, J=13.4, 17 Hz), 2.60 (1H, dd, J=2.7, 17.1 Hz), 1.94 (1H, dd, J=6.6, 13.4 Hz), 1.64 (1H, d, J=0.5 Hz), 1.43-1.41 (2H, m), 1.37-1.34 (2H, m), 1.13 (3H, s), 1.12 (3H, s); $^{13}$C-NMR (100 MHz, $CDCl_3$) 198.2 (s), 168.5 (s), 168.4 (s), 165.5 (s), 165.4 (s), 165.2 (s), 146.5 (s), 144.5 (s), 135.8 (s), 129.7 (s), 128.2 (s), 124.7 (d), 118.7 (d), 113.6 (d), 103.2 (s), 97.1 (d), 96.2 (d), 77.8 (d), 71.5 (s), 44.3 (t), 43.7 (t), 41.2 (t), 29.2 (q), 29.1 (q), 25.4 (t), 23.7 (t), 16.2 (t).

Example 6

3',4',5,7-Tetraacetyl Propolin D (34)

To a solution of Propolin D (compound 32, 124 mg, 0.29 mmol) in pyridine (4 mL) acetic anhydride (2 mL) was added and the reaction mixture was stirred at room temperature for 6 h. EtOAc (25 mL) was added to the reaction mixture and the mixture was washed with 0.1 N HCl (10 mL×3). The organic layer was dried over $Na_2SO_4$ and evaporated under reduced pressure to give a residue. The residue was purified by a silica gel column ($CH_2Cl_2$) to yield pure 34 oil (139 mg, 80%). $^1$H-NMR (400 MHz, $CDCl_3$) 7.49 (1H, d, J=8.6 Hz), 7.18 (1H, d, J=8.6 Hz), 6.72 (1H, d, J=2.2 Hz), 6.53 (1H, d, J=2.2 Hz), 5.60 (1H, dd, J=2.5, 13.8 Hz), 5.01 (1H, td, J=5.3, 4.6 Hz), 4.94 (1H, td, J=1.0, 5.8 Hz), 3.35 (1H, dd, J=7.1, 15.7 Hz), 3.26 (1H, dd, J=5.3, 15.5 Hz), 2.98 (1H, dd, J=13.8, 16.8 Hz), 2.36 (3H, s), 2.27 (6H, s), 2.26 (s, 3H), 2.02-1.91 (5H, m), 1.64 (3H, s), 1.62 (3H, s), 1.55 (3H, s); $^{13}$C-NMR (100 MHz, $CDCl_3$) 188.8 (s), 169.2 (s), 168.1 (s), 168.0 (s), 167.9 (s), 163.2 (s), 155.9 (s), 151.3 (s), 142.8 (s), 140.9 (s), 137.0 (s), 135.2 (s), 133.5 (s), 131.6 (s), 124.5 (d), 123.9 (d), 121.6 (d), 120.7 (d), 111.6 (s), 110.7 (d), 109.0 (d), 76.1 (d), 44.8 (t), 39.4 (t), 26.5 (t), 25.6 (t), 25.5 (q), 21.1 (q), 21.0 (q), 20.7 (q), 20.3 (q), 17.7 (q), 16.3 (q).

Example 7

3',4',5,7-Tetramethyl Propolin D (35)

To the mixture 32 (128 mg, 0.31 mmol), $K_2CO_3$ (431 mg, 3.1 mmol) and acetone (15 mL) $Me_2SO_4$ (0.25 mL, 2.48 mmol) was added and the resulting solution was heated to reflux under nitrogen for 24 h. After removal of the organic solvent, the residue was dissolved in $CH_2Cl_2$ (50 mL) and washed with $H_2O$ (50 mL×3). The organic layer was dried over $Na_2SO_4$ and evaporated under reduced pressure. The residue obtained was purified by a silica gel column (EtOAc: n-Hexane=1:4) to give compound 35 (107 mg, 72%). $^1$H-NMR (400 MHz, $CDCl_3$) 7.26 (1H, d, J=8.6 Hz), 6.85 (1H, d, J=8.6 Hz), 6.10 (1H, d, J=2.3 Hz), 6.07 (1H, d, J=2.3 Hz), 5.34 (1H, dd, J=2.6, 13.5 Hz), 5.04 (1H, td, J=5.3, 4.6 Hz), 4.99 (1H, td, J=1.0, 5.8 Hz), 3.88 (3H, s), 3.86 (3H, s), 3.80 (3H, s), 3.74 (3H, s), 3.46 (1H, dd, J=6.6, 15.2 Hz), 3.44 (1H, dd, J=5.8, 15.2 Hz), 3.02 (1H, dd, J=13.5, 16.5 Hz), 2.69

(1H, dd, J=2.6, 16.5 Hz), 2.00-1.97 (2H, m), 1.94-1.92 (2H, m), 1.65 (3H, s), 1.60 (3H, s), 1.52 (3H, s).

Example 8

3',4',7-O-Trimethylpropolin G (4)

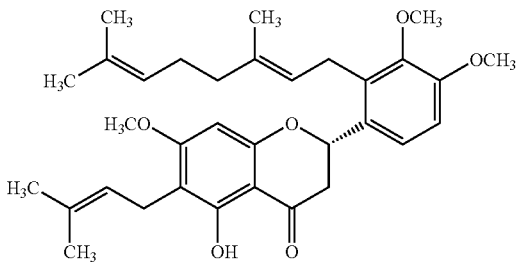

To the mixture of Propolin G (2.30 g, 2.75 mmol), K$_2$CO$_3$ (1.94 g, 13.99 mmol), and acetone (80 mL) Me$_2$SO$_4$ (2.17 mL, 17.35 mmol) was added and the resulting solution was stirred at rt for 0.5 h, and then heated to reflux under nitrogen for 6 h. After removal of the organic solvent, the residue was dissolved in CH$_2$Cl$_2$ (40 mL) and washed with H$_2$O (40 mL×3). The CH$_2$Cl$_2$ layers were dried over Na$_2$SO$_4$ and evaporated under reduced pressure. The residue obtained was purified by a silica gel column (EtOAc-n-Hexane=1:8) to give 4 (954 mg, 65%):

$^1$H-NMR (400 MHz, CDCl$_3$) □ 12.06 (1H, s), 7.26 (1H, d, J=8.4 Hz), 6.86 (1H, d, J=8.4 Hz), 6.03 (1H, s), 5.50 (1H, dd, J=2.4, 13.4 Hz), 5.17-5.14 (1H, m), 5.04-5.00 (2H, m), 3.87 (3H, s), 3.79 (3H, s), 3.79 (6H, s), 3.46-3.45 (2H, m), 3.25-3.23 (2H, m), 3.05 (1H, dd, J=13.5, 16.7 Hz), 2.70 (1H, dd, J=2.6, 16.7 Hz), 2.02-1.94 (7H, m), 1.75 (3H, s), 1.67 (3H, s), 1.66 (3H, s), 1.61 (3H, s), 1.58 (3H, s)

Example 9

6-(2-Hydroxy-2-methylbutyl)-2'-(7-hydroxy-3,7-dimethyloct-2-enyl)-5-hydroxy-3',4',7-trimethoxyflavanone (6d)

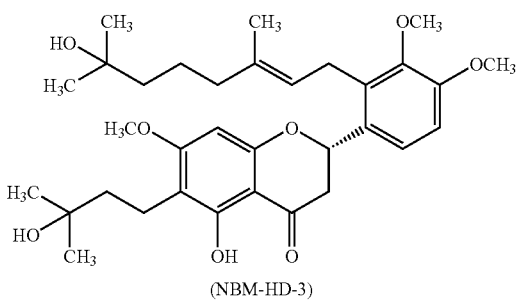

(NBM-HD-3)

To a solution of compound 4 (530 mg, 0.99 mmol) in THF (15 mL) 49% H$_2$SO$_4$ (10 mL) was added at ice bath. After complete addition, the reaction mixture was stirred at room temperature for 8 h and then diluted with H$_2$O. The reaction mixture was extracted with CH$_2$Cl$_2$ (30 mL×3). The combined organic layers were dried over Na$_2$SO$_4$ and evaporated under reduced pressure to give a residue, which was purified by a silica gel column (n-hexane:EtOAc=1:1) to give pure oil 6d (191 mg, 34%). $^1$H-NMR (400 MHz, CDCl$_3$) □ 12.06 (1H, brs), 7.27 (1H, d, J=8.6 Hz), 6.86 (1H, d, J=8.6 Hz), 6.05 (1H, s), 5.50 (1H, dd, J=2.6, 13.6 Hz), 5.03 (1H, t, J=6.2 Hz), 3.87 (3H, s), 3.80 (6H, s), 3.48 (1H, dd, J=5.5, 15.2 Hz), 3.42 (1H, dd, J=6.1, 15.2 Hz), 3.06 (1H, dd, J=13.6, 17.1 Hz), 2.70 (1H, dd, J=2.7, 17.1 Hz), 2.65-2.61 (2H, m), 1.95-1.92 (2H, m), 1.65 (3H, s), 1.41-1.35 (5H, m), 1.26 (6H, s), 1.15 (3H, s), 1.14 (3H, s).

Example 10

Other Compounds

The following two compounds are prepared according to the methods as stated above.

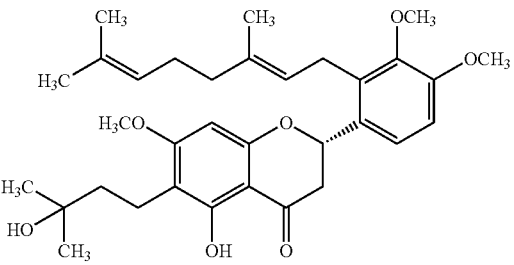

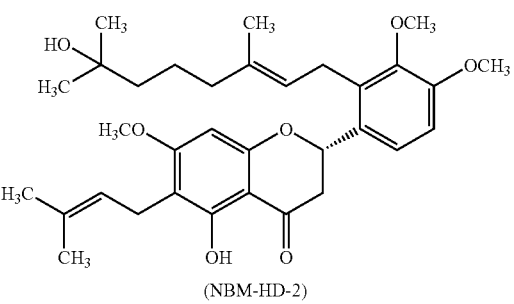

(NBM-HD-2)

Example 11

Inhibition of Cancer Cell Growth by the Compound of the Invention (NBM-HD-1)

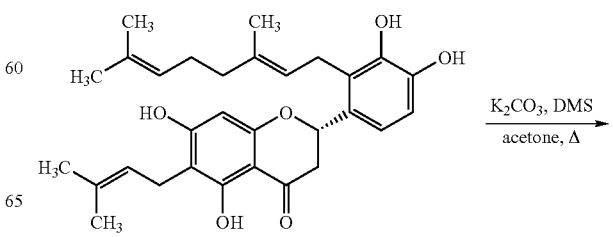

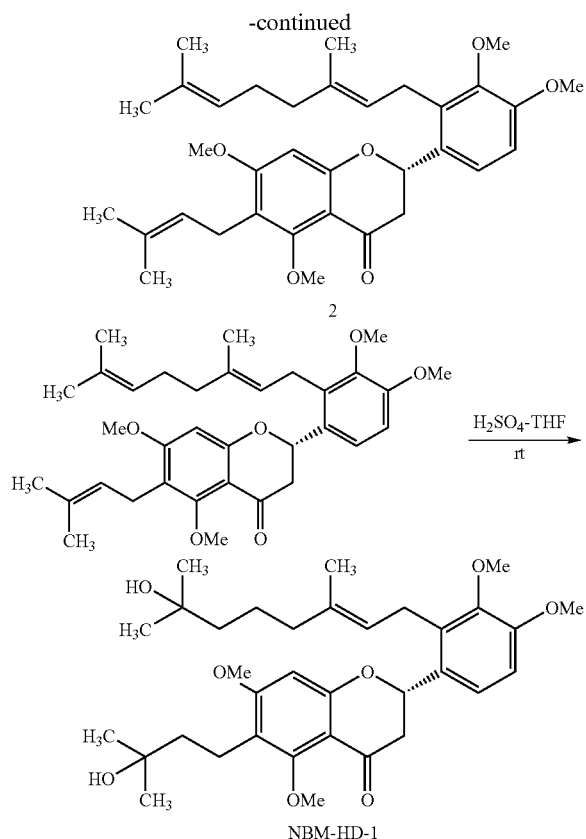

The cancer cell line, rat C6 glioma cells, was cultured in Dulbecco's modified Eagle's medium (DMEM; Gibco) supplemented with penicillin G, streptomycin sulphate, 0.5 mM of L-glutamine and 10% fetal bovine serum (FBS; Gibco) at 37° C., 5% $CO_2$ and 95% relative humidity. For all experiments, the cells were seeded at a density of $3\times10^5$ per well in 6-well plates. After 24 hours, the cells were treated with different concentrations of the compound NBM-HD-1 (i.e., the compound of formula III depicted herein). After 48 hours, the cells were observed and counted. According to the results shown in FIG. 1, NBM-HD-1 can arrest the growth of rat C6 glioma cells. After the C6 glioma cells were incubated with 2.5 μg/mL (see FIG. 1(A)-b), 5 μg/mL (see FIG. 1(A)-c) and 10 μg/mL (see FIG. 1(A)-d) of NBM-HD-1 for 48 hours, the density of the cells reduced dramatically in comparison with that of control (see FIG. 1(A)-a). The results obtained by cell counting showed the same tendency (see FIG. 1(B)). The above-mentioned results indicate that NBM-HD-1 can inhibit the growth of C6 glioma cells in a dose-dependent manner.

Figure 2:
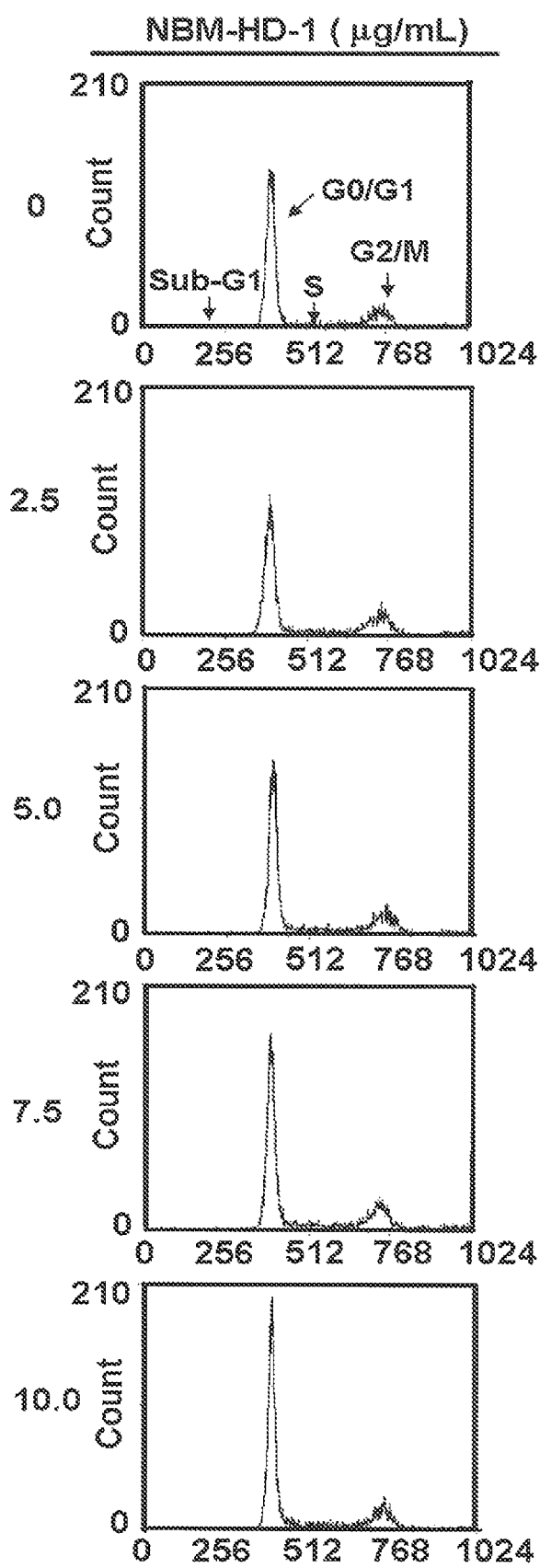
FIG. 2 shows the DNA contents of the rat glioma C6 cells analyzed by FACScan Cytometry.

$1\times10^6$ of rat C6 glioma cells were treated with various concentrations of NBM-HD-1 (0 μg/mL, 2.5 μg/mL, 5 μg/mL, and 10 μg/mL) for 72 hours. The treated cells were trysinized and collected. The cells were resuspended in 200 μL PBS and then fixed by adding 800 μL of cold 100% ethanol. The resulting cells were fixed overnight at −20□. The cell pellets were collected by centrifugation, resuspended in 1 mL of hypotonic buffer (0.5% Triton X-100 in PBS and 1 μg/mL RNase A), and incubated at 37□ for 30 minutes. Then, 1 mL of PI solution (50 μg/mL) was added to the resulting cell pellets. The mixture was allowed to stand at 4□ for 30 min. The DNA amounts of the cells were analyzed by FACScan Cytometry (Becton Dickinson) (see FIG. 2). The results of FIG. 2 showed that NBM-HD-1 can significantly inhibit C6 glioma cell growth through modulating the cell cycle arrest on the G0/G1 phase in a dose-dependent manner.

Example 12

Inhibition of Cell Growth and Induction of Differentiation of Cancer Cells by the Compound of the Invention (NBM-HD-1)

Figure 3:
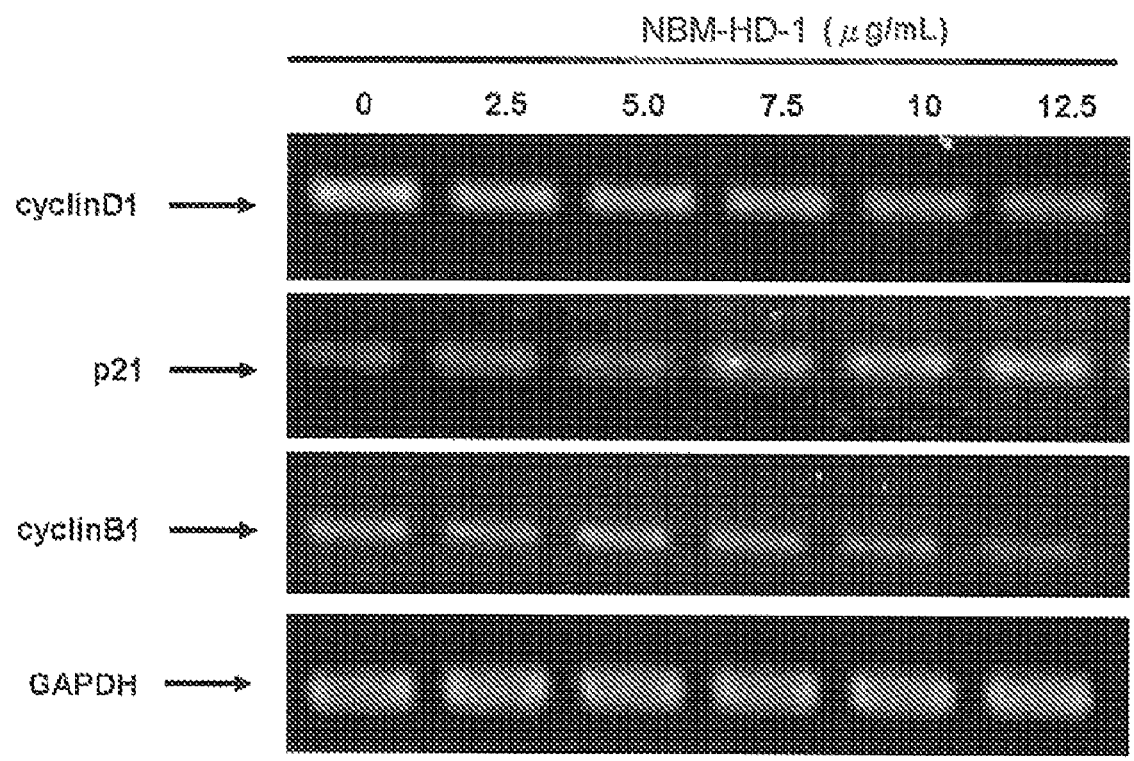
FIG. 3 shows the electrophoresis plot of the genes of cell cycle of the rat glioma C6 cells treated with different doses of NBM-HD-1.

For the rat C6 glioma cells, the cell cycle related to mRNA expression was examined by RT-PCR. The total RNAs were isolated from the treated C6 cells by using the RNeasy Mini Kit (Qiagen) according to the manufacturer's instructions. The cDNAs were produced from 500 ng of total RNAs using ReverTra-Plus-™ (TOYOBO). The RT product (1 μl) was amplified by PCR with primers to analyze several genes of cell cycle by using GAPDH as an internal control. The results were shown in FIG. 3. According to the results of FIG. 3, NBM-HD-1 can modulate the expression of some cell cycle regulators. The results showed that NBM-HD-1 can decrease the expression of cyclinD1 and cyclinB1 in a dose-dependent manner. On the contrary, the expression of p21 was increased.

After the C6 glioma cells were incubated with 10 μg/mL NBM-HD-1 for 24 hours, they were fixed and analyzed by the traditional immuno-fluorescent staining method. Staining of glia was carried out by using glial-specific GFAP antibody (SIGMA) as the primary antibody and a fluorescence labeled rabbit immuno-globulin (SIGMA) as the secondary antibody to bind with the primary antibody. The cells which are GFAP-positive were excited by a specific light source to emit fluorescence. Also, the nuclei were stained with DAPI. The staining results were shown in FIG. 4(A). According to FIG. 4(A), NBM-HD-1 can induce the GFAP expression of C6 glioma cancer cells. In contrast with the control group, more GFAP proteins were detected in the photos of the cells being treated with 10 μg/mL of NBM-HD-1. The middle row showed the photos of the cells with DAPI staining in FIG. 4(A).

Figure 4:
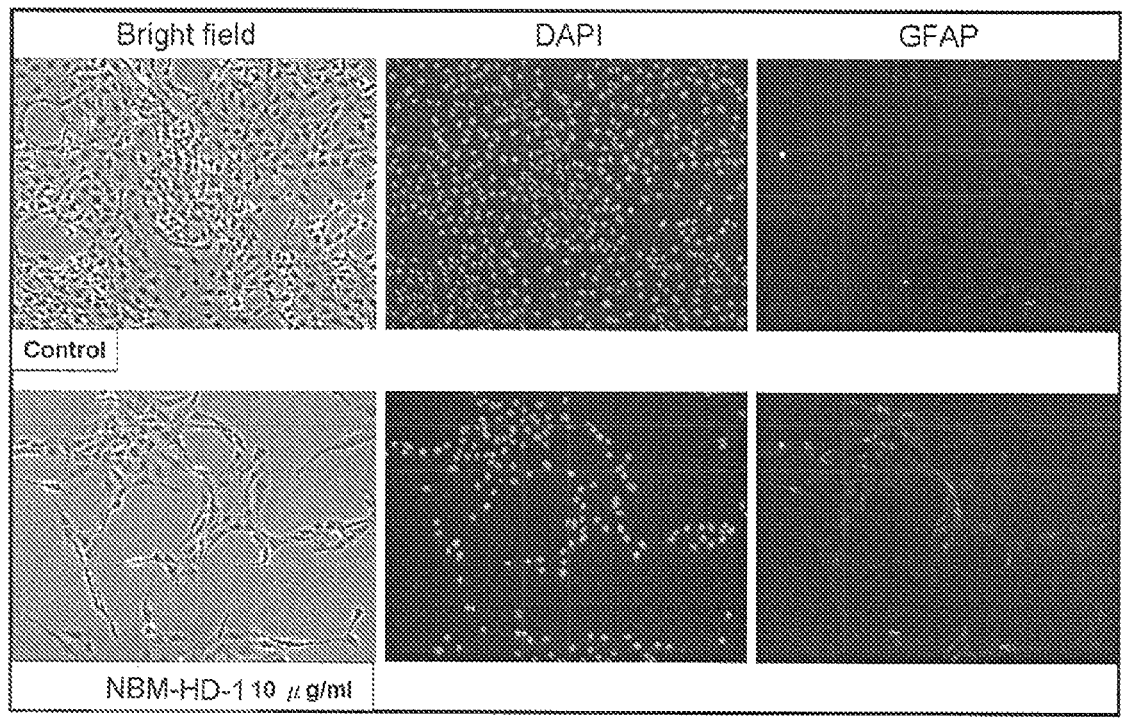
FIG. 4 shows the immuno-fluorescent staining photographs and RT-PCR data of the rat glioma C6 cells treated with NBM-HD-1.
Figure 4:
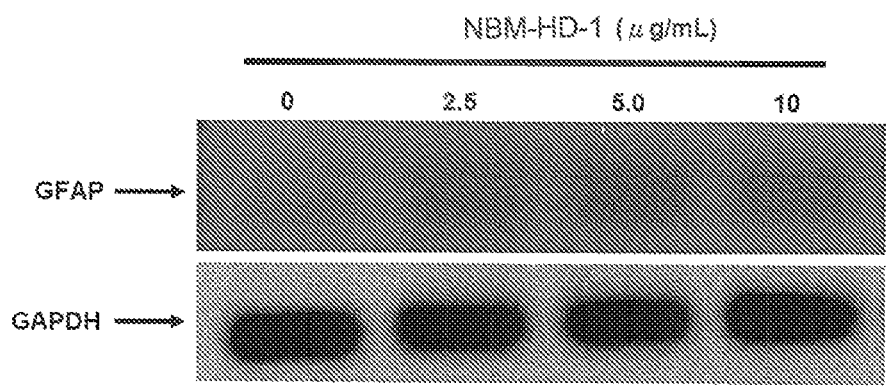

The GFAP mRNA expression was examined by RT-PCR. The results of FIG. 4(B) showed that the expression of GFAP was increased in a dose-dependent manner. These results indicated that NBM-HD-1 can induce the cell differentiation of C6 glioma cancer cells according to the increase of GFAP expression.

Example 13

Increase of the Accumulation of Hyperacetylated Histone in the Cancer Cells Treated with the Compound of the Invention (NBM-HD-1)

Figure 5:
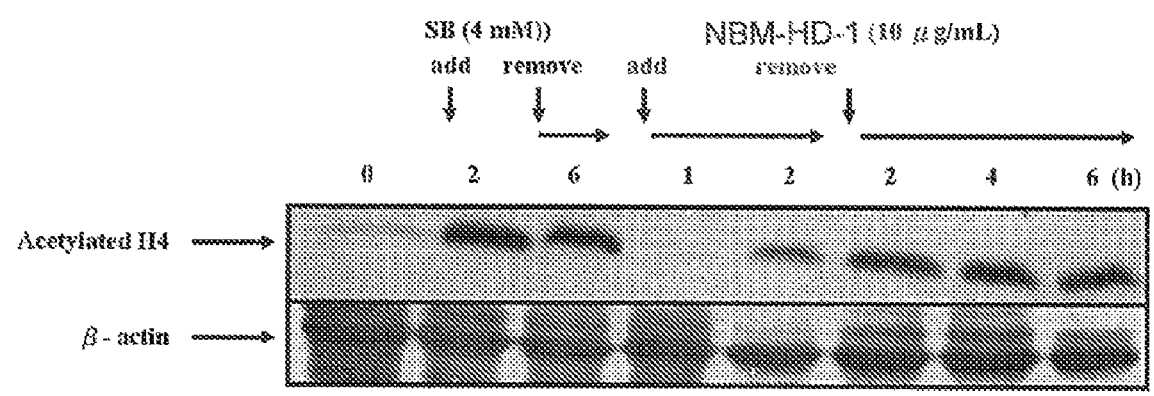
FIG. 5 shows Western Blotting plot of the rat glioma C6 cells treated with NBM-HD-1 and sodium butyrate.

Accumulation of hyperacetylated histone H4 was analyzed in the cell lysates by using Western Blotting and the antibody directed against acetylated histone H4 (Upstate). The C6 glioma cells were seeded at a density of $1\times10^6$ per 10 cm culture dish. After 24 hours, the cells were treated with 10 μg/mL of NBM-HD-1 or 4 mM sodium butyrate for several hours. The whole-cell lysates were prepared by using denaturing SDS sample buffer and then separated on 15% SDS-polyacrylamide gels. As shown in FIG. 5, both sodium butyrate and NBM-HD-1 can increase the accumulation of hyperacetylated histone H4. The amount of acetylated histones was hardly detectable in untreated C6 glioma cells. The amount of acetylated histone H4 of the cells treated with 4 mM sodium butyrate for 2 hours increased. Sodium butyrate was then removed from the culture medium. After 6 hours, the amount of acetylated histone H4 decreased. The accumulation of acetylated histone H4 increased in the cells treated with NBM-HD-1 for 2 hours. After removal of NBM-HD-1, the amount of acetylated histone H4 increased over time. The highest histone acetylation appeared at 6 hours after the compound had been removed. These results indicated that, similar to sodium butyrate, NBM-HD-1 is an HDAC inhibitor. Because NBM-HD-1 is more hydrophobic than sodium butyrate, NBM-HD-1 can be retained in the cells longer than sodium butyrate and continuously induce the acetylation of histone H4.

Example 14

Inhibition of HDAC Activity by the Compound of the Invention (NBM-HD-1)

Figure 6:
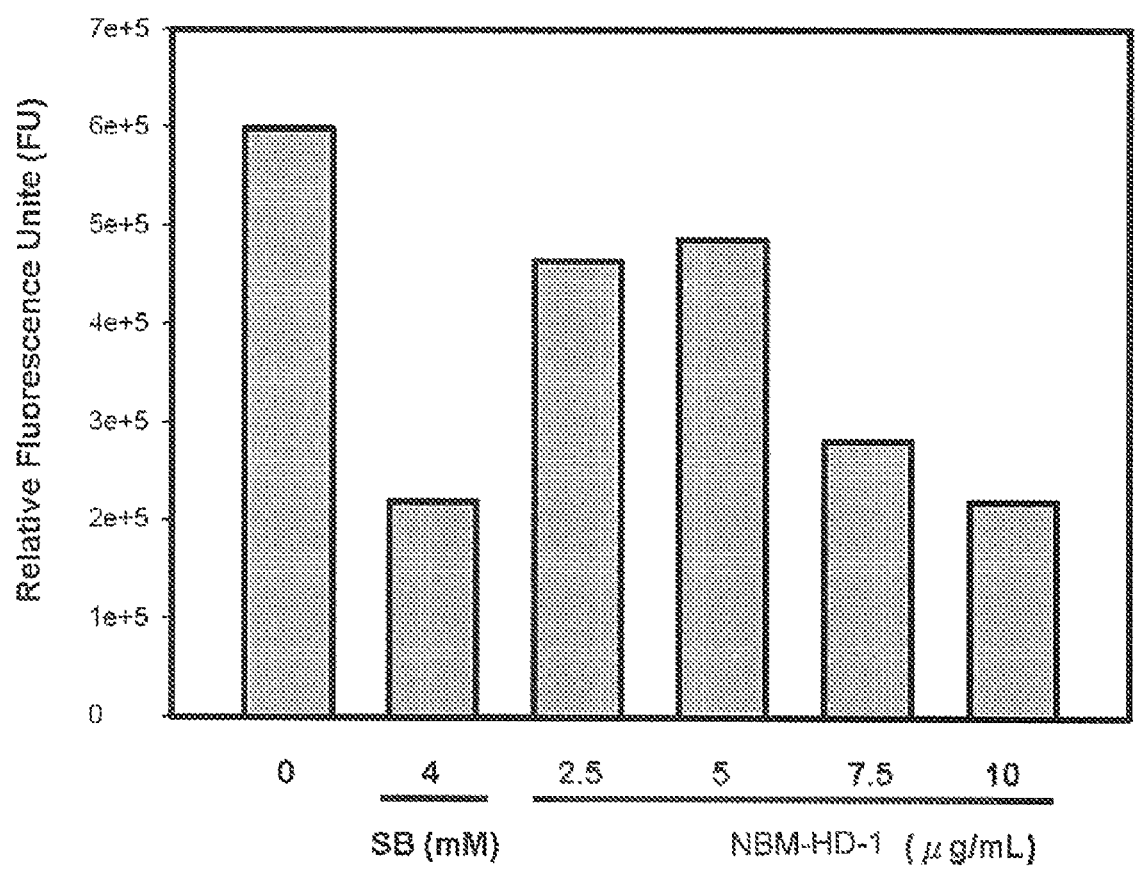
FIG. 6 shows the relative inhibited activity of the HDAC on the rat glioma C6 cells treated with NBM-HD-1 and sodium butyrate.

The C6 glioma cells were treated with different doses of NBM-HD-1 and sodium butyrate (SB). After 24 hours, the cells were harvested to extract the nuclear proteins by Nuc-Buster™ Protein Extraction Kit (Novagen) as described by the manufacturer's instructions. These extracts were then used in HDAC Activity Assay Kit (Calbiochem) to analyze their HDAC (histone deacetylase) inhibition activities. The HDAC fluorometric substrate, which comprises an acetylated lysine side chain, was incubated with extracted nuclear protein first. Deacetylation of the substrate sensitized the substrate, so that, in the second step, treatment with the Lysine Developer produced a fluorophore. The fluorophore can easily be analyzed by using a fluorescence plate reader. As shown in FIG. 6, NBM-HD-1 can inhibit the HDAC activity in C6 glioma cells. Inhibition of HDAC has been implicated in the induction of differentiation in cancer cells. In this experiment, a well-known compound for HDAC inhibition, sodium butyrate, was used as a positive control. The lower fluorescence unit showed higher HDAC inhibition activity in the experimental group. The results indicated that NBM-HD-1 significantly inhibits HDAC activity.

Example 15

Inhibition of HDAC Activity and Change of the Morphology of Cancer Cells by the Compound of the Invention (NBM-HD-1)

Figure 7:
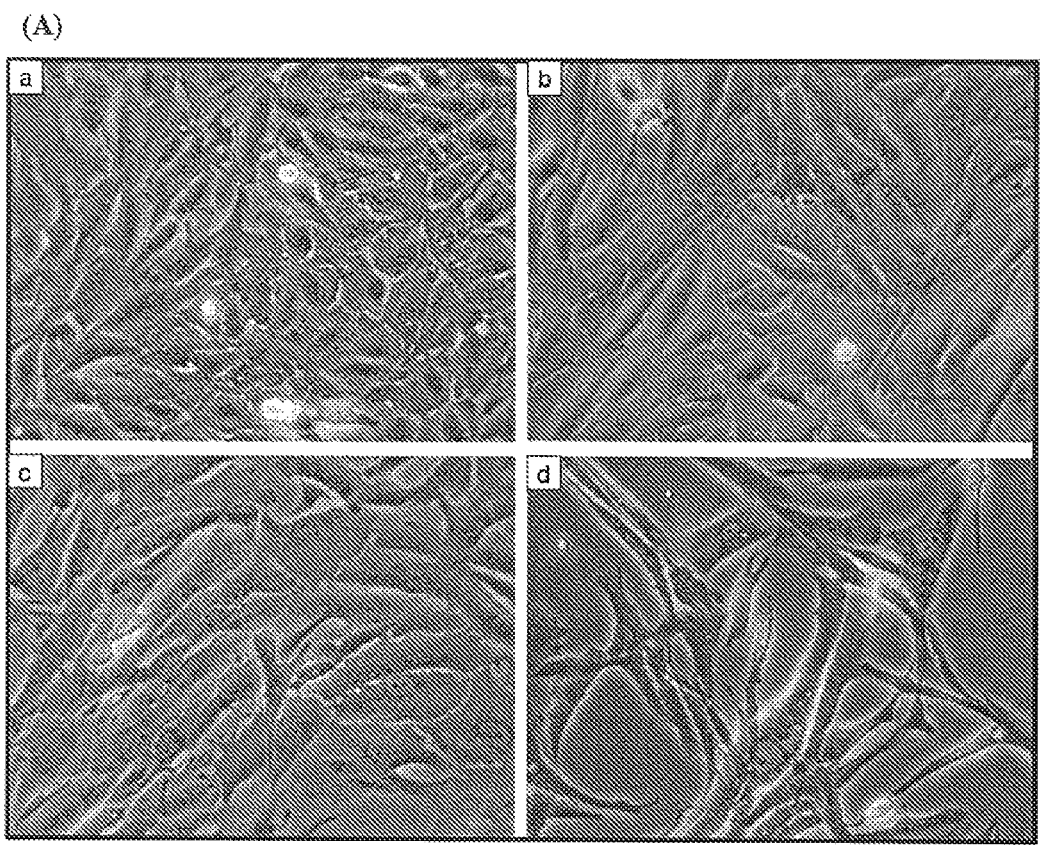
FIG. 7 shows the microscopic photographs of the human giloblastoma DBTRG-05MG cancer cells treated with different doses of NBM-HD-1.
Figure 7:
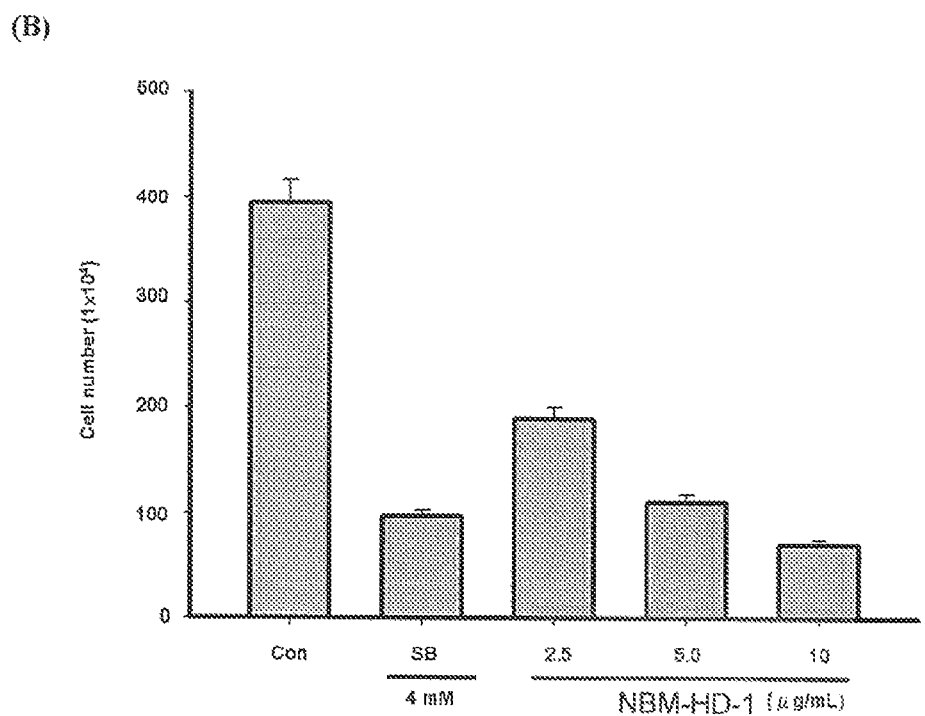

The human giloblastoma DBTRG-05MG cancer cells were cultured in RPMI medium 1640 (Gibco) supplemented with penicillin G, streptomycin sulphate, 0.5 mM of L-glutamine and 10% fetal bovine serum (FBS; Gibco), 100 mh/L sodium pyruvate (Gibco), and 1% NEAA (Gibco) at 37° C., 5% $CO_2$ and 95% relative humidity. For these experiments, the cells were seeded at a density of $3 \times 10^5$ per well of 6-well plates. After 24 hours, the cells were treated with different concentrations of NBM-HD-1 and 4 mM sodium butyrate. The cells were observed and counted after 72 hours. As shown in FIG. 7, NBM-HD-1 significantly inhibited the growth of 05MG cancer cells and changed the morphology of the cells. In 05MG cells (FIG. 7(A)), after incubation with 2.5 μg/mL (FIG. 7(A)-*b*), 5 μg/mL (FIG. 7(A)-*c*) and 10 μg/mL (FIG. 7(A)-*d*) of NBM-HD-1 for 72 hours, the density of the cells reduced dramatically in comparison with that of the control group (FIG. 7(A)-*a*). The 05MG cells in the experimental group also changed to become longer than those in the control group. The results of the cell counting (FIG. 7(B)) indicated that sodium butyrate could inhibit the proliferation of 05MG cancer cells, and so could NBM-HD-1. These results indicate that NBM-HD-1 can inhibit the growth of 05MG cells in a dose-dependent manner and change the morphology of 05MG cancer cells.

Figure 8:
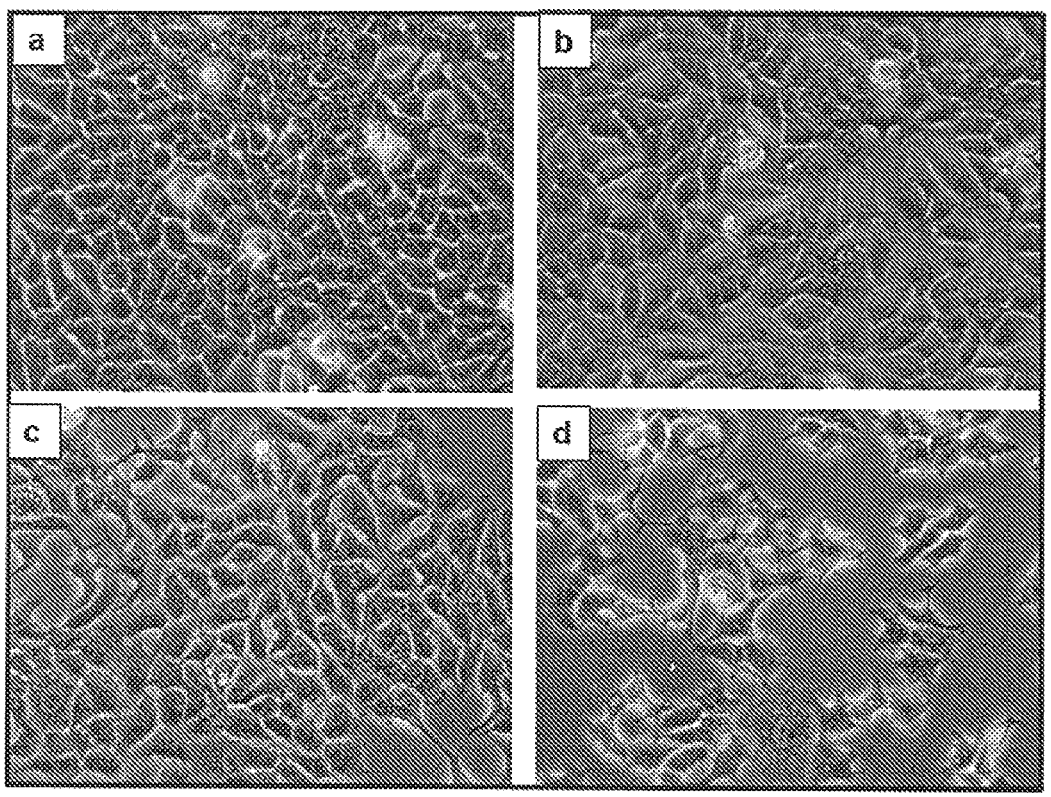
FIG. 8 shows the microscopic photographs of the human breast MCF-7 cancer cells treated with different doses of NBM-HD-1.
Figure 8:
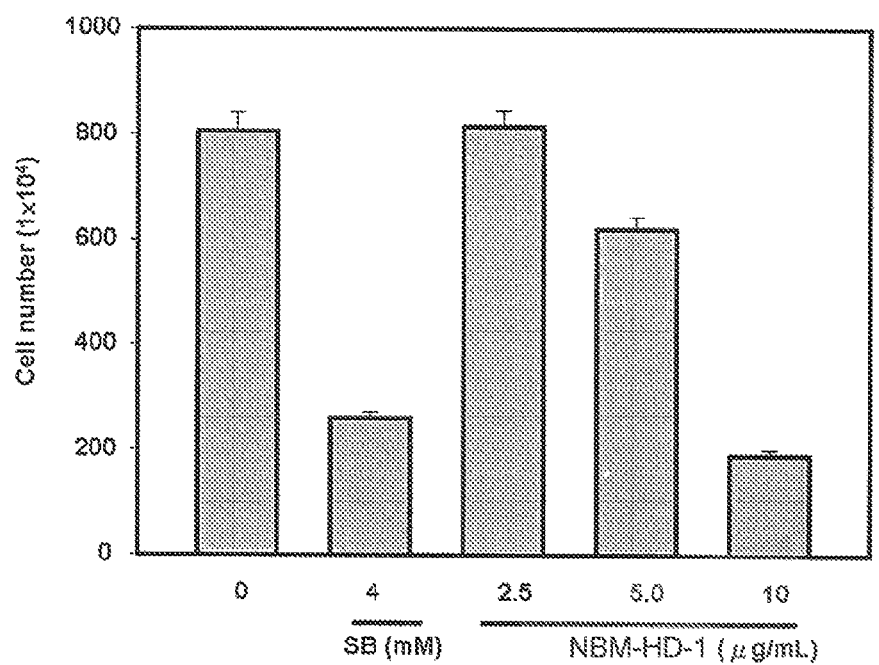

The breast cancer MCF-7 cells, were cultured in Dulbecco's modified Eagle's medium (DMEM; Gibco) supplemented with penicillin G, streptomycin sulphate, 0.5 mM of L-glutamine and 10% fetal bovine serum (FBS; Gibco) at 37° C., 5% $CO_2$ and 95% relative humidity. The cells were seeded at a density of $3 \times 10^5$ per well of 6-well plates. After 24 hours, the cells were treated with different concentrations of compound NBM-HD-1 and 4 mM sodium butyrate being used as the positive control. The cells were observed after 48 hours and counted after 96 hours. As shown in FIG. 8, NBM-HD-1 significantly inhibits the growth of MCF-7 cancer cells and changes the morphology of the cells. In FIG. 8(A), after the cells were incubated with 2.5 μg/mL (FIG. 8(A)-*b*), 5 μg/mL (FIG. 8(A)-*c*) and 10 μg/mL (FIG. 8(A)-*d*) of NBM-HD-1 for 48 hours, the density of MCF-7 cells reduced dramatically in comparison with that of the control group (FIG. 8(A)-*a*). The morphology of the MCF-7 cells in the experimental group changed in comparison with that in the control group. FIG. 8(B), and showed that 4 mM sodium butyrate was able to inhibit the growth of MCF-7 cells. The results of the cell counting (FIG. 8(B)) indicate that, similar to sodium butyrate, NBM-HD-1 inhibits cell growth. These results indicate that NBM-HD-1 can inhibit the growth of MCF-7 cancer cells in a dose-dependent manner and change their morphology.

Figure 9:
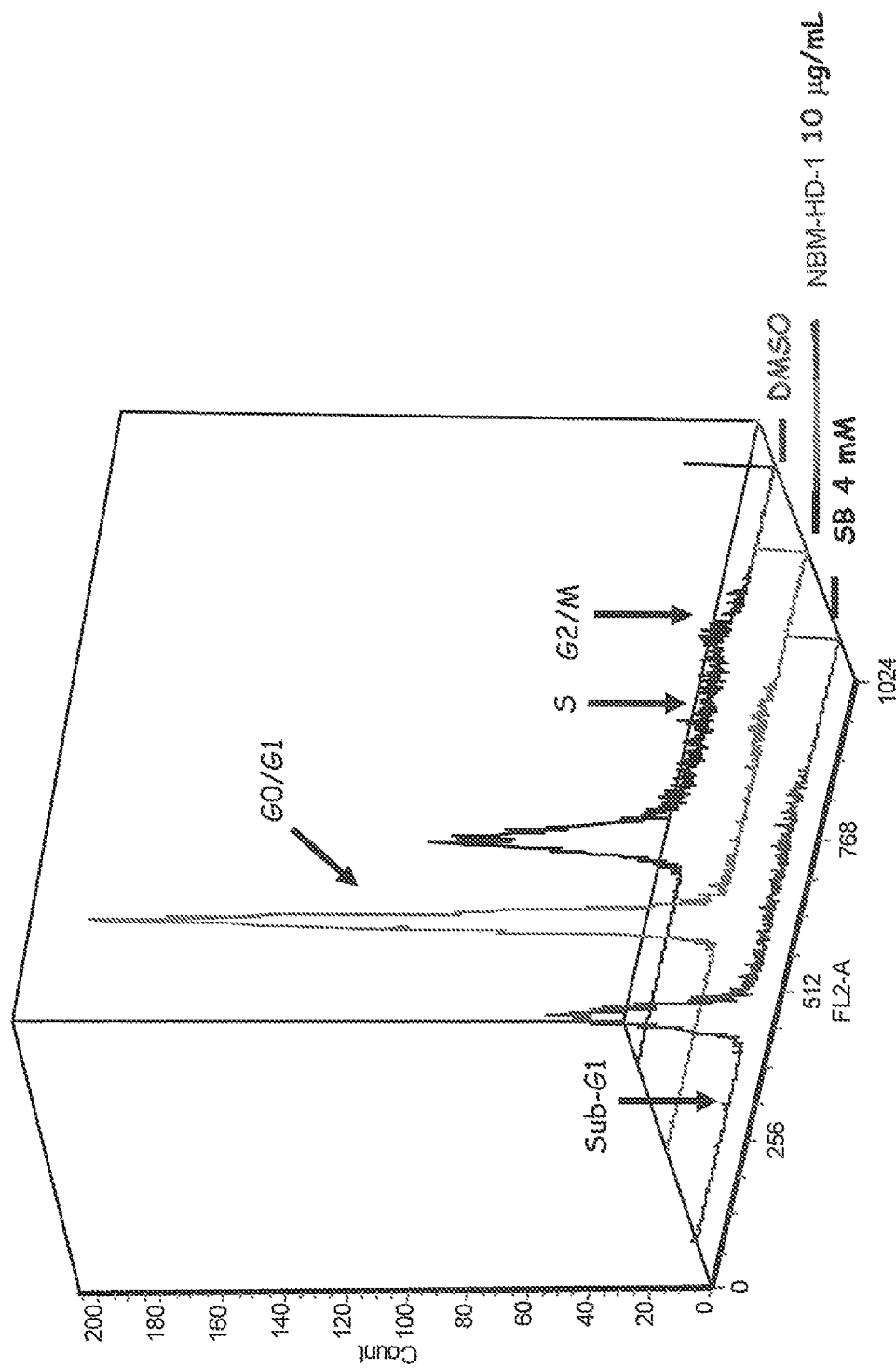
FIG. 9 shows that NBM-HD-1 markedly inhibited the MCF-7 cell growth via modulation of the cell cycle arrested on the G0/G1 phase in a dose-dependent manner.

MCF-7 cancer cells ($1 \times 10^6$) in a 100-mm dish were treated with various concentrations of NBM-HD-1 (0, 2.5, 5, and 10 μg/mL) or 4 mM sodium butyrate for 72 hours. The DNA of the cells was then analyzed by FACScan cytometry (Becton Dickinson). As shown in FIG. 9, NBM-HD-1 markedly inhibited MCF-7 cell growth via modulation of the cell cycle, arrested on the G0/G1 phase in a dose-dependent manner. The percentage of G0/G1 phase increased from 74.46 to 92.55 in a dose-dependent manner. It was also found that NBM-HD-1 significantly decreased both S and G2/M phases of the cells in a dose-dependent manner.

Figure 10:
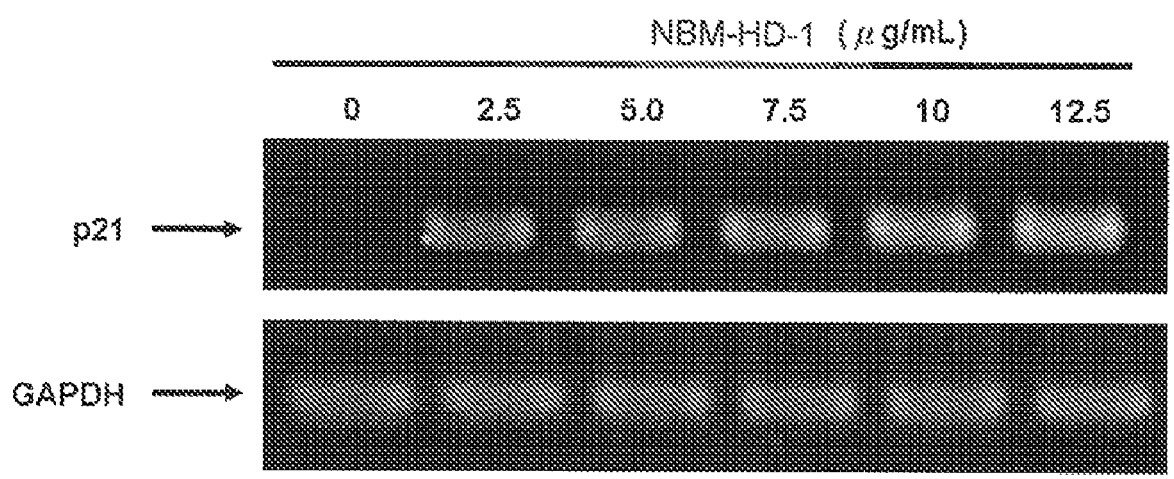
FIG. 10 shows that NBM-HD-1 markedly increased the p21$^{WAF1/CIP1}$ gene expression in a dose-dependent manner.

The cell cycle related to p21 mRNA expression was examined by RT-PCR. The total RNAs were isolated from the treated MCF-7 cells and used in the RT reaction. cDNA (1 μl) was used as a template to amplify p21 gene by PCR. GAPDH was used as an internal control. As shown in FIG. 10, NBM-HD-1 can increase the p21 mRNA expression in MCF-7 cancer cells. In this experiment, MCF-7 cells were treated with different doses of NBM-HD-1 for 24 hours. The results indicated that NBM-HD-1 induced the expression of p21 in a dose-dependent manner.

Figure 11:
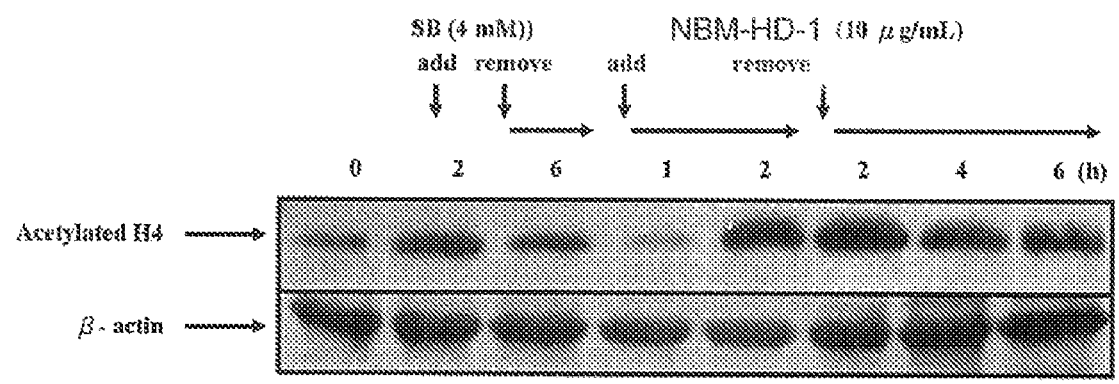
FIG. 11 shows Western Blotting plot of the MCF-7 cell treated with NBM-HD-1.

Accumulation of hyperacetylated histone H4 was analyzed in the cell lysates by using Western Blotting and an antibody that binds to acetylated histone H4 (Upstate). The MCF-7 cancer cells were seeded at a density of $1 \times 10^6$ per 10 cm culture dish. After 24 hours, the cells were treated with 10 μg/mL of NBM-HD-1 or 4 mM sodium butyrate for several hours. The HDAC inhibition by NBM-HD-1 was tested by analyzing the degree of histone acetylation with a specific antibody for hyperacetylated histone H4. The sodium butyrate was used as a positive control. As shown in FIG. 11, the results with MCF-7 cells were similar to those with C6 glioma cells.

Example 16

Enhancing the Neurite Outgrowth by the Compound of the Invention (NBM-HD-1)

The growth medium for the NSCs (neural stem cells) and cortical neurons was prepared by adding penicillin G, streptomycin and 0.5 mM of L-glutamine into a B-27 supplemented neurobasal medium (Gibco). The unborn fetus was taken out of the fetal sac in the abdominal cavity of a 17-day pregnant Wistar rat under anesthesia. The cerebral tissue was removed from the fetus and treated with 0.1% trypsin solution at 25° C. for three minutes. After washing with PBS solution 3 times, the cells were dissociated by up and down mixing. The resulting solution was passed through a 70 μm Nylon cell strainer (Falcon) in order to obtain the filtrate that contained cerebral cells. The filtrate was centrifuged at 1000 rpm for 10 minutes and the supernatant was aspirated. The resulting pellet was resuspended in the growth medium prepared as stated above. The resulting suspension contained NSCs.

The cells obtained from the suspension were cultivated in 6-well plates coated with 30 μg/ml of poly-D-lysine (Sigma) at the density of 75 cells/mm$^2$. The cells were cultured at 37° C., 5% $CO_2$ and 95% relative humidity. The growth media contained 0.63 μg/mL of NBM-HD-1 and the growth media with 1 μl of DMSO was used as the control. The differentiated cells after cultivation were categorically called cortical neurons.

Figure 12:
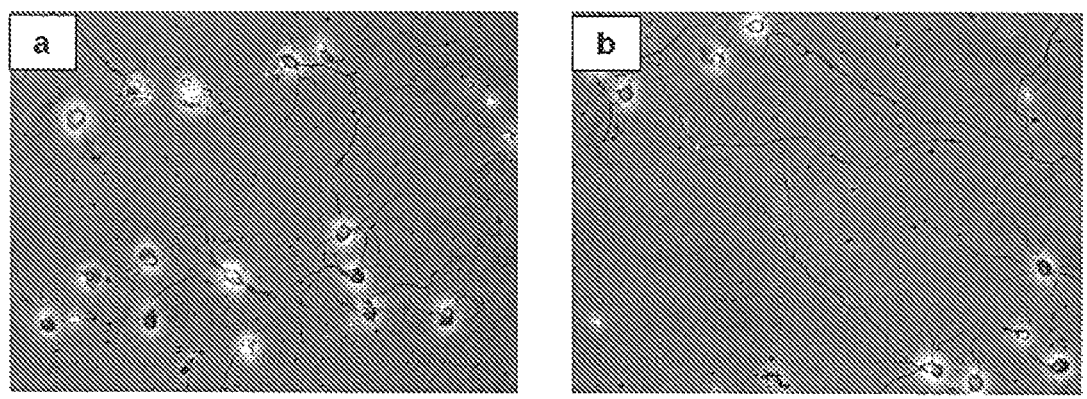
FIG. 12 shows the photographs of the neurite outgrowth of the cortical neurons treated with NBM-HD-1.
Figure 12:
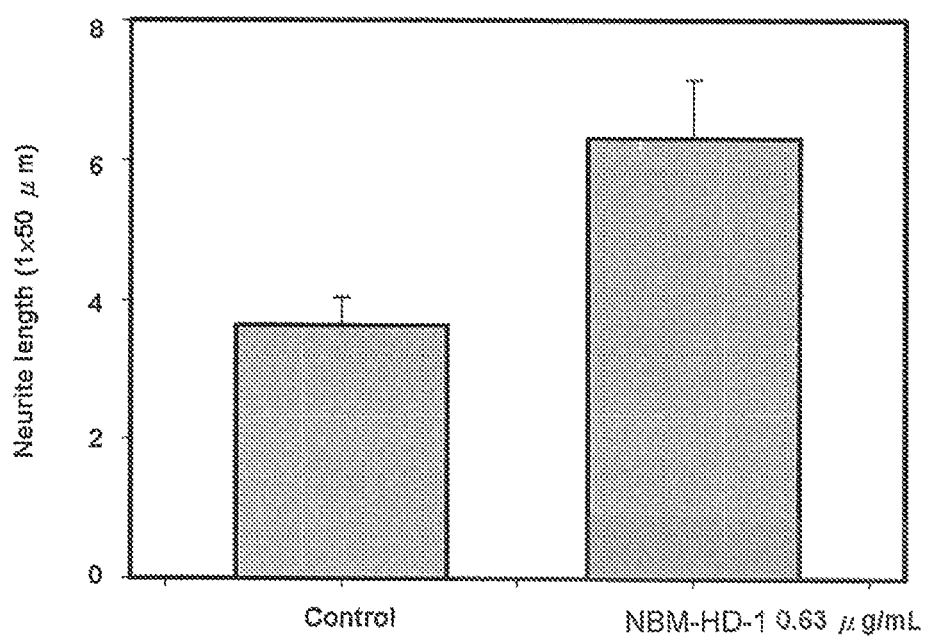

After cultivation for 6 days, live cells were observed by microscope. The lengths of the neurites of the neurons in 6 different fields were measured and averaged. As shown in FIG. 12, NBM-HD-1 could promote the neurite outgrowth. In FIG. 12, the length of the neurites of the experimental group (FIG. 12(A)-*b*) is longer than that of the control group (FIG. 12(A)-*a*). After measuring the lengths of the neurites, the result indicated that the average length of the neurites of the experiment group was greater than that of the control group (FIG. 12(B)).

Example 17

Inhibition of Cancer Cell Growth by the Compound of the Invention (NBM-HD-2)

Figure 13:
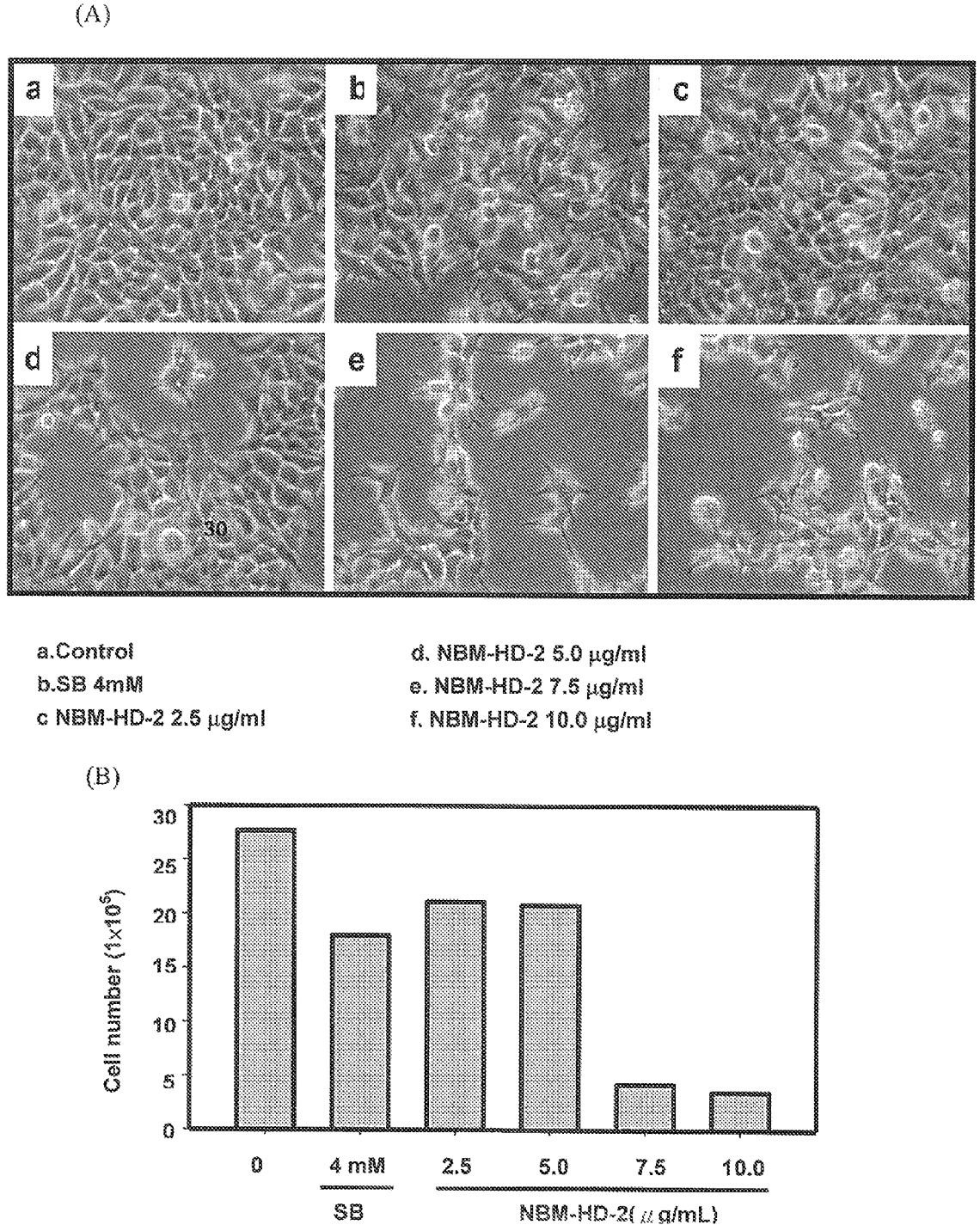
FIG. 13 shows the microscopic photographs of the human breast cancer MCF-7 cells treated with different concentrations of NBM-HD-2.

MCF-7 cancer cells were seeded at a density of 3×10$^5$ per well in 6-well plates. After 24 hours, the cells were treated with different concentrations of compound NBM-HD-2 and 4 mM sodium butyrate being used as the positive control. The cells were observed and counted after 72 hours. As shown in FIG. 13, NBM-HD-2 significantly inhibits the growth of MCF-7 cancer cells and changes the morphology of the cells. In FIG. 13(A), after the cells were incubated with 2.5 μg/mL (FIG. 13(A)-*c*), 5 μg/mL (FIG. 13(A)-*d*), 7.5 μg/mL (FIG. 13(A)-*e*) and 10 μg/mL (FIG. 13(A)-*f*) of NBM-HD-2 for 72 hours, the density of MCF-7 cells reduced dramatically in comparison with that of the control group (FIG. 13(A)-*a*). The morphology of the MCF-7 cells in the experimental group changed in comparison with that in the control group. FIG. 13(A) showed that 4 mM sodium butyrate was able to inhibit the growth of MCF-7 cells. The results of the cell counting (FIG. 13(B)) indicated that, similar to sodium butyrate, NBM-HD-2 inhibited cell growth. These results indicate that NBM-HD-2 can inhibit the growth of MCF-7 cancer cells in a dose-dependent manner and change their morphology.

Example 18

Inhibition of Cancer Cell Growth by the Compounds of the Invention (NBM-HD-3)

Figure 14:
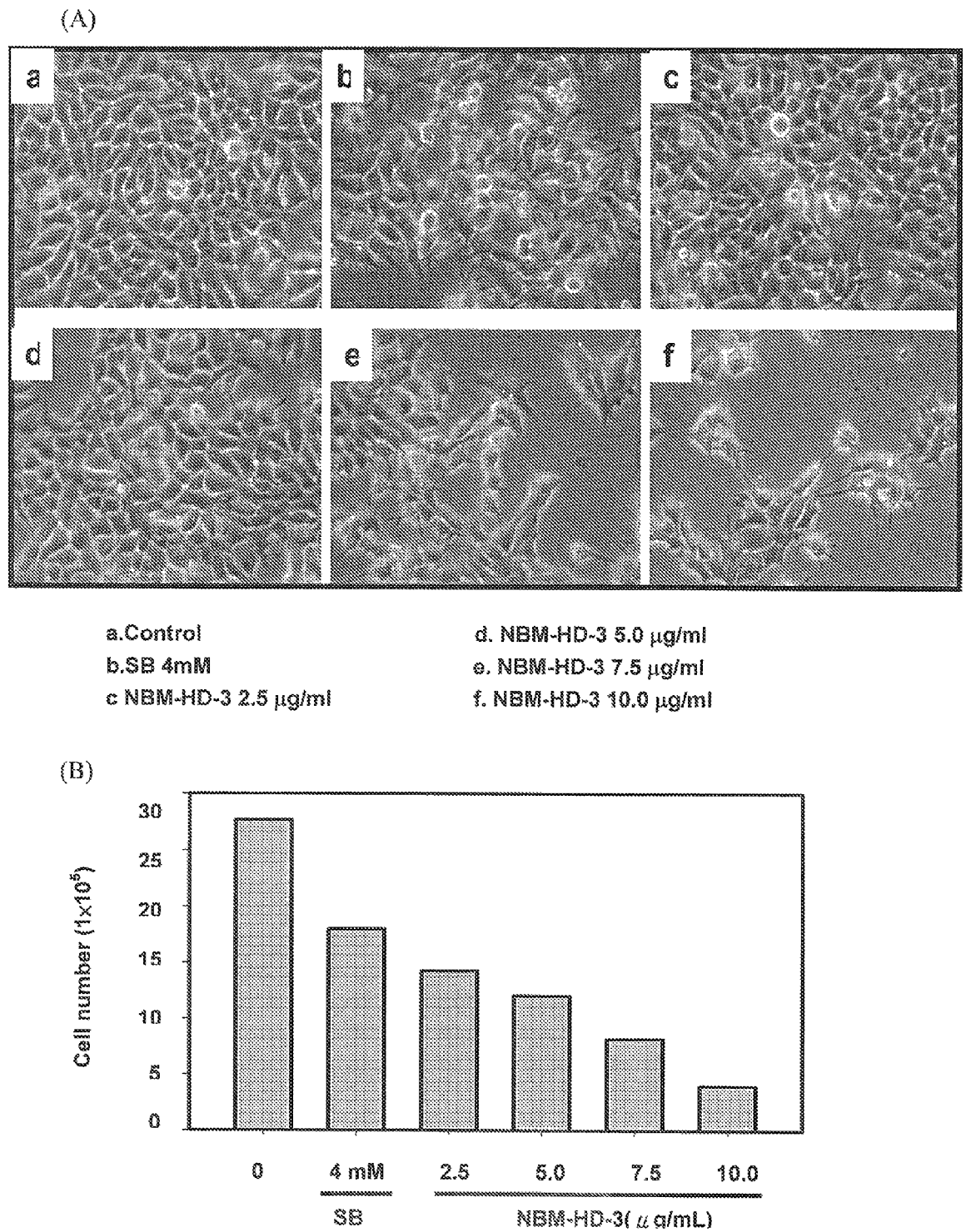
FIG. 14 shows the microscopic photographs of the human breast cancer MCF-7 cells treated with different concentrations of NBM-HD-3.

MCF-7 cancer cells were seeded at a density of 3×10$^5$ per well of 6-well plates. After 24 hours, the cells were treated with different concentrations of compound NBM-HD-3 and 4 mM sodium butyrate, which was being used as the positive control. The cells were observed and counted after 72 hours. As shown in FIG. 14, NBM-HD-3 significantly inhibits the growth of MCF-7 cancer cells and changes the morphology of the cells. In FIG. 14(A), after the cells were incubated with 2.5 μg/mL (FIG. 14(A)-*c*), 5 μg/mL (FIG. 14(A)-*d*), 7.5 μg/mL (FIG. 14(A)-*e*) and 10 μg/mL (FIG. 14(A)-*f*) of NBM-HD-3 for 72 hours, the density of MCF-7 cells reduced dramatically in comparison with that of the control group (FIG. 14(A)-*a*). The morphology of the MCF-7 cells in the experimental group changed in comparison with that in the control group. FIG. 14(A) showed that 4 mM sodium butyrate was able to inhibit the growth of MCF-7 cells. The results of the cell counting (FIG. 14(B)) indicate that, similar to sodium butyrate, NBM-HD-3 inhibits cell growth. These results indicate that NBM-HD-3 can inhibit the growth of MCF-7 cancer cells in a dose-dependent manner and change their morphology.

What is claimed is:
1. A compound represented by the following formula (I):

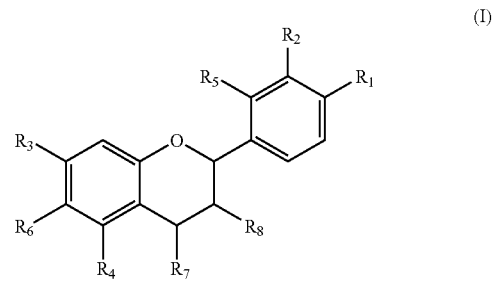

wherein
$R_1$ and $R_2$ are each independently O-alkyl, S-alkyl, N-alkyl, O-alkenyl, S-alkenyl, N-alkenyl, O-alkynyl, S-alkynyl, N-alkynyl, O—$C_{3-8}$cycloalkyl, S—$C_{3-8}$cycloalkyl, N—$C_{3-8}$cycloalkyl, O-unsaturated 5- to 10-membered monocyclic or bicyclic ring, S-unsaturated 5- to 10-membered monocyclic or bicyclic ring, N-unsaturated 5- to 10-membered monocyclic or bicyclic ring, alkyl, alkylenyl, alkynyl, $C_{3-8}$cycloalkyl, an unsaturated 5- to 10-membered monocyclic or bicyclic ring or a saturated or unsaturated 5- to 10-membered heterocyclic ring comprising at least one ring heteroatom selected from the group consisting of: N, O and S; or $R_1$ and $R_2$ can together form dioxolane;
$R_3$ is O-alkyl, S-alkyl, N-alkyl, O-alkenyl, S-alkenyl, N-alkenyl, O-alkynyl, S-alkynyl, N-alkynyl, O—$C_{3-8}$cycloalkyl, S—$C_{3-8}$-cycloalkyl, N—$C_{3-8}$cycloalkyl, O-unsaturated 5- to 10-membered monocyclic or bicyclic ring, S-unsaturated 5- to 10-membered monocyclic or bicyclic ring, N-unsaturated 5- to 10-membered monocyclic or bicyclic ring, alkyl, alkylenyl, alkynyl, $C_{3-8}$cycloalkyl, an unsaturated 5- to 10-membered monocyclic or bicyclic ring or a saturated or unsaturated 5- to 10-membered heterocyclic ring comprising at least one ring heteroatom selected from the group consisting of: N, O and S;
$R_4$ is OH, OC(=O)alkyl, O-alkyl, S-alkyl, N-alkyl, O-alkenyl, S-alkenyl, N-alkenyl, O-alkynyl, S-alkynyl, N-alkynyl, O—$C_{3-8}$cycloalkyl, S—$C_{3-8}$cycloalkyl, N—$C_{3-8}$cycloalkyl, O-unsaturated 5- to 10-membered monocyclic or bicyclic ring, S-unsaturated 5- to 10-membered monocyclic or bicyclic ring, N-unsaturated 5- to 10-membered monocyclic or bicyclic ring, alkyl, alkylenyl, alkynyl, $C_{3-8}$cycloalkyl, an unsaturated 5- to 10-membered monocyclic or bicyclic ring or a saturated or unsaturated 5- to 10-membered heterocyclic ring comprising at least one ring heteroatom selected from the group consisting of: N, O and S;

$R_5$ is $C_{4-16}$ alkyl or $C_{4-16}$ alkenyl unsubstituted or substituted with one or more OH, halogen, CN, NO, $N_3$, $NH_2$, CHO, $OR_9$, $SR_9$, $NR_9$, or $COOR_9$;

$R_6$ is $C_{2-12}$ alkyl or $C_{2-12}$ alkenyl unsubstituted or substituted with one or more OH, halogen, CN, NO, $N_3$, $NH_2$, CHO, $OR_9$, $SR_9$, or $NR_9$;

$R_7$ is hydrogen, halogen, OH, $NH_2$, COOH, CHO, CN, NO, =O, or $R_7$ and $R_8$ may together form a double bond, a $C_{3-6}$ cycloalkyl, or a 5- to 10-membered heterocyclic ring comprising at least a heteroatom selected from the group consisting of N, O and S;

$R_8$ is hydrogen, halogen, OH, $NH_2$, COOH, CHO, CN or NO;

$R_9$ is phenyl, C(=O)$R^{10}$ or C(=O)O$R^{10}$; and $R^{10}$ is OH, NHOH or $NH_2$;

wherein both $R_5$ and $R_6$ are not simultaneously unsubstituted alkyl or alkenyl;

or pharmaceutically acceptable salts, stereoisomers, enantiomers, prodrugs or solvates thereof.

2. The compound according to claim 1, wherein $R_1$ and $R_2$ are each independently $OC_{1-6}$alkyl, O-phenyl or O-benzyl or $R_1$ and $R_2$ together form dioxalene.

3. The compound according to claim 2, wherein $R_1$ and $R_2$ are each independently $OCH_3$, $OCH_2CH_3$, $OCH_2CH_2CH_3$, O-phenyl or O-benzyl.

4. The compound according to claim 1, wherein $R_1$ and $R_2$ together form dioxolane.

5. The compound according to claim 1, wherein $R_3$ and $R_4$ are each independently $OC_{1-6}$alkyl, O-phenyl or O-benzyl.

6. The compound according to claim 1, wherein $R_3$ and $R_4$ are each independently $OCH_3$, $OCH_2CH_3$, $OCH_2CH_2CH_3$, O-phenyl or O-benzyl.

7. The compound according to claim 1, wherein $R_5$ is

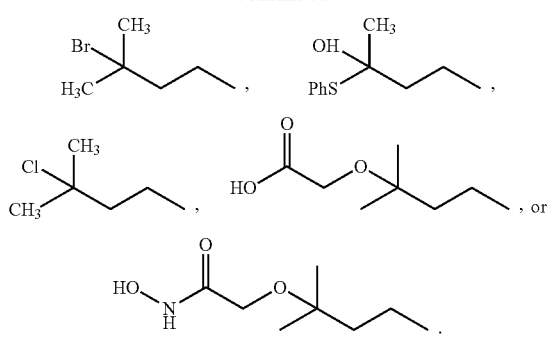

8. The compound according to claim 1, wherein $R_6$ is

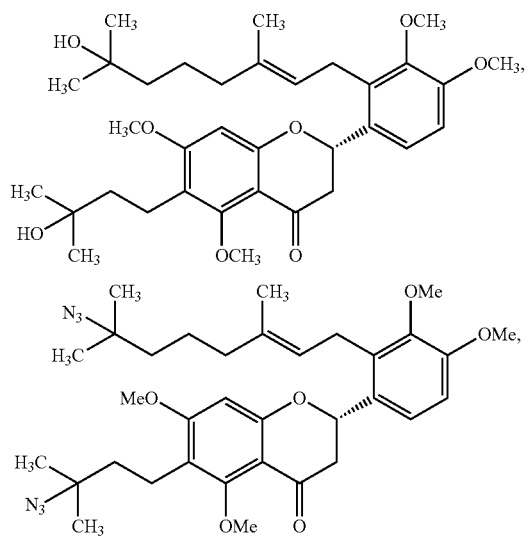

9. The compound according to claim 1, which is selected from the group consisting of:

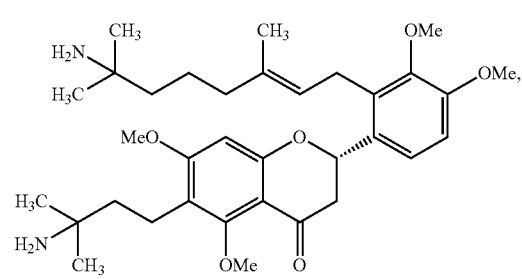

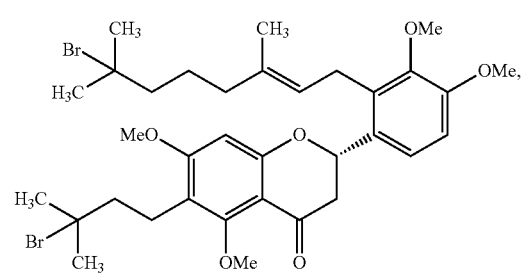

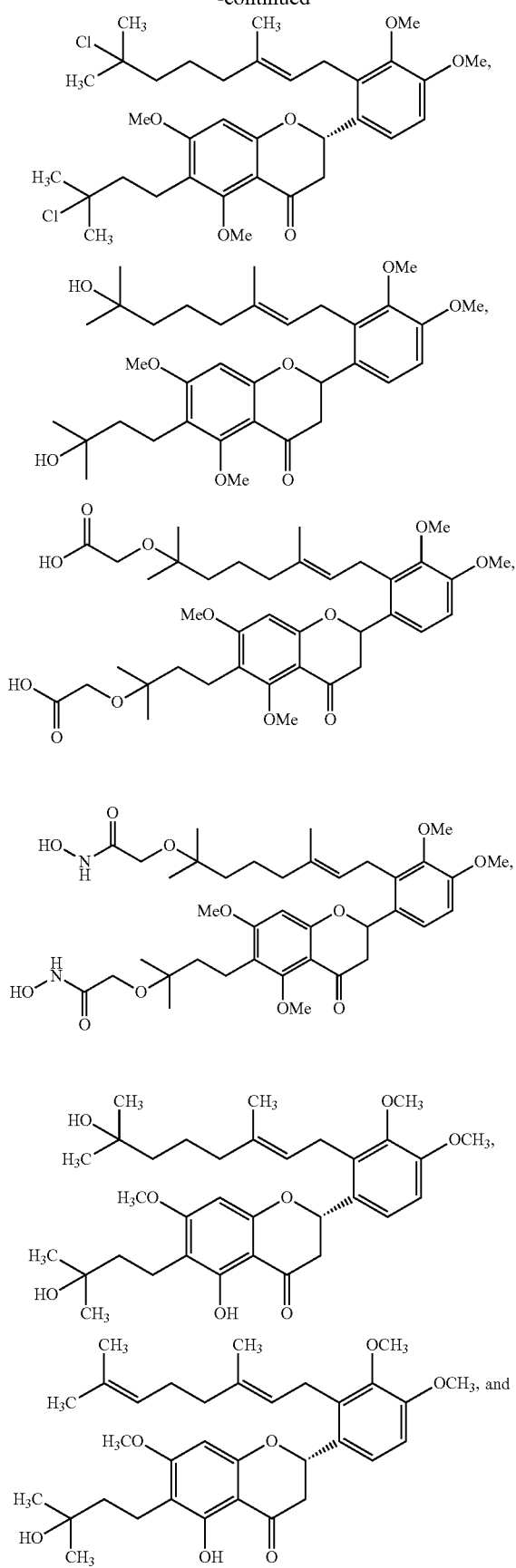
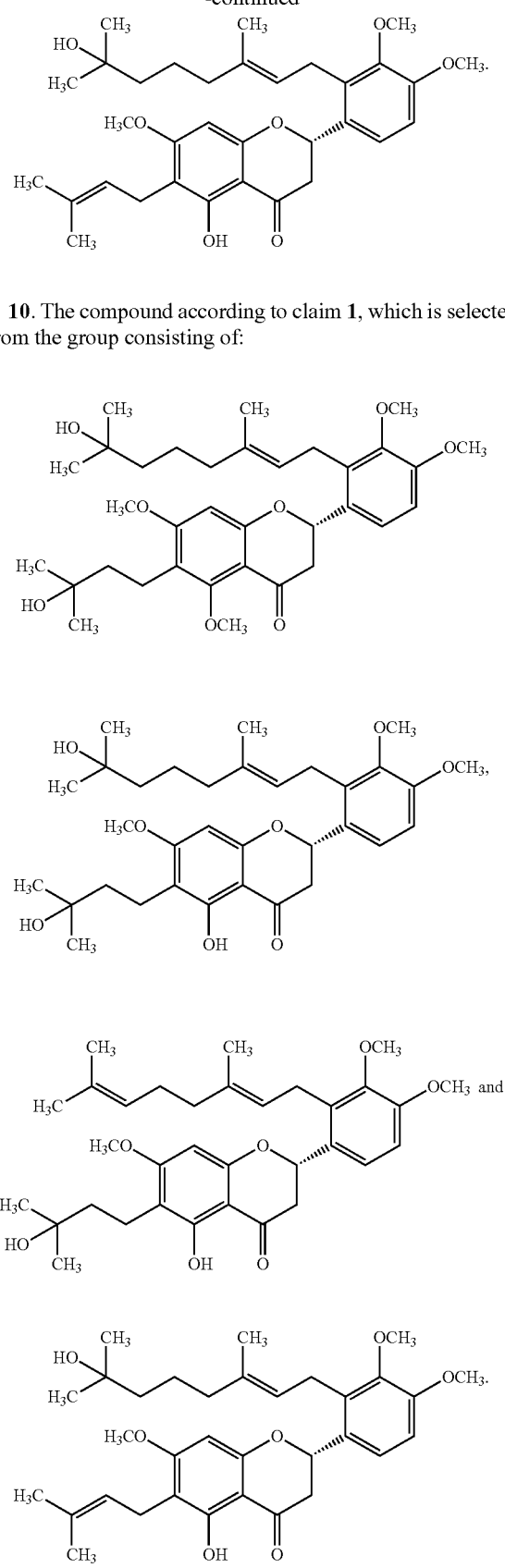
10. The compound according to claim 1, which is selected from the group consisting of:

11. A stereoisomer of the compound of formula (I) as defined in claim 1, which is represented by the following formula (II):

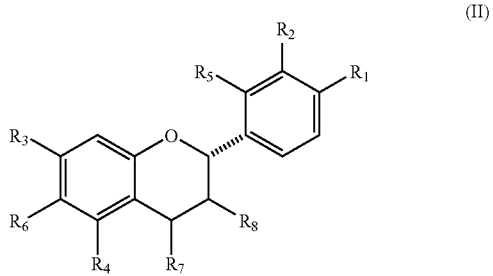

(II)

wherein $R_1$, $R_2$, $R_3$, $R_4$, $R_5$, $R_6$, $R_7$ and $R_8$ are defined as those in formula (I).

12. A pharmaceutical composition comprising the compound of claim 1 or pharmaceutically acceptable salts, stereoisomers, enantiomers, prodrugs or solvates thereof as an active ingredient and a pharmaceutically acceptable carrier.

13. A method of inhibiting histone deacetylase (HDAC) in a subject, which comprises administering to said subject a therapeutically effective amount of the compound of claim 1 or pharmaceutically acceptable salts, stereoisomers, enantiomers, prodrugs or solvates thereof.

14. A method of treating tumor or cell proliferative disease in a subject, which comprises administering to said subject a therapeutically effective amount of the compound of claim 1 or pharmaceutically acceptable salts, stereoisomers, enantiomers, prodrugs or solvates thereof.

15. A method of enhancing the neurite outgrowth in a subject, which comprises administering to said subject a therapeutically effective amount of the compound of claim 1 or pharmaceutically acceptable salts, stereoisomers, enantiomers, prodrugs or solvates thereof.

16. A method of treating neurodegenerative diseases and human spinal muscular atrophy (SMA) in a subject, which comprises administering to said subject a therapeutically effective amount of the compound of claim 1 or pharmaceutically acceptable salts, stereoisomers, enantiomers, prodrugs or solvates thereof.

* * * * *